US008165671B2

(12) United States Patent
Freeman et al.

(10) Patent No.: US 8,165,671 B2
(45) Date of Patent: Apr. 24, 2012

(54) AUTOMATIC THERAPY ADVISOR

(75) Inventors: Gary A. Freeman, Newton Center, MA (US); James E. Brewer, Lino Lakes, MN (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 11/136,327

(22) Filed: May 24, 2005

(65) Prior Publication Data

US 2006/0025824 A1 Feb. 2, 2006

(51) Int. Cl.
*A61N 1/39* (2006.01)

(52) U.S. Cl. ............ 607/5; 600/508; 600/509; 600/515; 600/518; 607/4; 607/6; 128/920; 128/923; 128/924; 706/924

(58) Field of Classification Search .......... 600/508–509, 600/515, 518; 607/4–6; 128/920, 923, 924, 128/897–898; 706/924
See application file for complete search history.

(56) References Cited

U.S. PATENT DOCUMENTS 4,059,099 A 11/1977 Davis
4,088,138 A 5/1978 Diack et al.
RE30,372 E 8/1980 Mirowski et al.
4,296,755 A 10/1981 Judell
4,355,634 A 10/1982 Kanter
4,588,383 A 5/1986 Parker et al.
4,610,254 A 9/1986 Morgan et al.
4,619,265 A 10/1986 Morgan et al.
4,680,708 A 7/1987 Ambos et al.
4,781,200 A * 11/1988 Baker ........................... 600/483
4,928,674 A 5/1990 Halperin et al.
4,947,857 A 8/1990 Albert et al.
5,077,667 A 12/1991 Brown et al.
5,092,341 A 3/1992 Kelen
5,109,862 A 5/1992 Kelen et al.
5,247,945 A 9/1993 Heinze et al.
5,285,792 A 2/1994 Sjoquist et al.
RE34,800 E 11/1994 Hutchins
(Continued)

FOREIGN PATENT DOCUMENTS

EP 1057451 12/2000
(Continued)

OTHER PUBLICATIONS

Aase et al., "Compression Depth Estimation for CPR Quality Assessment Using DSP on Accelerometer Signals," IEEE Transactions on Biomedical Engineering, vol. 49, No. 3, Mar. 2002.
(Continued)

*Primary Examiner* — Carl H Layno
*Assistant Examiner* — Deborah Malamud
(74) *Attorney, Agent, or Firm* — Fish & Richardson P.C.

(57) ABSTRACT

A method of automatically determining which type of treatment is most appropriate for (or the physiological state of) a patient. The method comprises transforming one or more time domain measurements from the patient into frequency domain data representative of the frequency content of the time domain measurements; processing the frequency domain data to form a plurality of spectral bands, the content of a spectral band representing the frequency content of the measurements within a frequency band; forming a weighted sum of the content of the spectral bands, with different weighting coefficients applied to at least some of the spectral bands; determining the type of treatment (or physiological state) based on the weighted sum.

23 Claims, 8 Drawing Sheets

200
202 Set segment-counter 0
204 Acquire 1 segment of ECG data
206 Apply a 0.5Hz High-pass filter
208 Do FFT
210 Quantification of the spectral shape
212 Increase segment-counter by 1
214 Enough Number of ECG Segments? No
Yes 216
Process Final EFV score
218 Final EFV score below threshold? No
Yes
220 Estimate Arrhythmic State

U.S. PATENT DOCUMENTS 5,365,426 A 11/1994 Siegel et al.
5,391,187 A 2/1995 Freeman
5,439,483 A 8/1995 Duong-Van
5,466,244 A 11/1995 Morgan
5,471,991 A 12/1995 Shinnar
5,474,574 A 12/1995 Payne et al.
5,496,257 A 3/1996 Kelly
5,511,553 A 4/1996 Segalowitz
5,555,889 A * 9/1996 Karagueuzian et al. ...... 600/518
5,562,710 A 10/1996 Olsen et al.
5,589,639 A 12/1996 Antonio et al.
5,591,213 A 1/1997 Morgan
5,611,815 A 3/1997 Cole et al.
5,617,853 A 4/1997 Morgan
5,619,265 A 4/1997 Suzuki et al.
5,645,571 A 7/1997 Olson et al.
5,662,690 A 9/1997 Cole et al.
5,674,253 A 10/1997 Adams et al.
5,683,424 A 11/1997 Brown et al.
5,700,281 A 12/1997 Brewer et al.
5,735,879 A 4/1998 Gliner et al.
5,755,671 A 5/1998 Albrecht et al.
5,772,604 A 6/1998 Langberg et al.
5,957,856 A * 9/1999 Weil et al. .................... 600/518
5,967,995 A * 10/1999 Shusterman et al. ......... 600/516
6,125,298 A 9/2000 Olson et al.
6,125,299 A 9/2000 Groenke et al.
6,171,257 B1 1/2001 Weil et al.
6,174,295 B1 1/2001 Cantrell et al.
6,178,357 B1 1/2001 Gliner et al.
6,188,928 B1 2/2001 Noren et al.
6,224,562 B1 5/2001 Lurie et al.
6,246,907 B1 6/2001 Lin et al.
6,263,238 B1 7/2001 Brewer et al.
6,289,243 B1 9/2001 Lin et al.
6,306,107 B1 10/2001 Myklebust et al.
6,308,094 B1 10/2001 Shusterman et al.
6,351,671 B1 2/2002 Myklebust et al.
6,360,125 B1 3/2002 Weil et al.
6,390,996 B1 5/2002 Halperin et al.
6,393,316 B1 5/2002 Gillberg et al.
6,418,342 B1 7/2002 Owen et al.
6,427,685 B1 8/2002 Ray, II
6,438,419 B1 8/2002 Callaway et al.
6,480,734 B1 11/2002 Zhang et al.
6,496,731 B1 12/2002 Lovett
6,597,943 B2 7/2003 Taha et al.
6,622,036 B1 * 9/2003 Suffin .......................... 600/544
6,622,042 B1 9/2003 Thacker
6,658,290 B1 12/2003 Lin et al.
6,671,545 B2 12/2003 Fincke
6,687,540 B2 2/2004 Marcovecchio
6,697,671 B1 2/2004 Nova et al.
6,807,442 B1 10/2004 Myklebust et al.
6,827,695 B2 12/2004 Palazzolo et al.
6,961,612 B2 11/2005 Elghazzawi et al.
6,990,373 B2 1/2006 Jayne et al.
6,993,386 B2 1/2006 Lin et al.
7,006,865 B1 2/2006 Cohen et al.
7,013,176 B2 * 3/2006 Ding et al. ........................ 607/9
7,032,596 B2 4/2006 Thompson et al.
7,085,601 B1 8/2006 Bardy et al.
7,089,055 B2 8/2006 Cates et al.
7,220,235 B2 5/2007 Geheb et al.
2001/0047140 A1 11/2001 Freeman
2002/0026131 A1 2/2002 Halperin
2002/0055694 A1 5/2002 Halperin et al.
2002/0133197 A1 9/2002 Snyder et al.
2002/0165471 A1 11/2002 Halperin et al.
2002/0165585 A1 11/2002 Dupelle et al.
2002/0193711 A1 12/2002 Halperin et al.
2003/0023277 A1 1/2003 Owen et al.
2003/0083586 A1 5/2003 Ferek-Petric
2003/0088285 A1 5/2003 Marcovecchio et al.
2003/0130697 A1 7/2003 Halperin et al.
2003/0144699 A1 7/2003 Freeman
2003/0195567 A1 * 10/2003 Jayne et al. ...................... 607/5
2004/0049234 A1 3/2004 Morgan et al.
2004/0059237 A1 3/2004 Narayan et al.
2004/0162585 A1 8/2004 Elghazzawi et al.
2004/0171954 A1 9/2004 Holman
2004/0210172 A1 10/2004 Palazzolo et al.
2004/0215244 A1 10/2004 Marcovecchio et al.
2004/0267324 A1 12/2004 Geheb et al.
2005/0021094 A1 1/2005 Ostroff et al.
2005/0027317 A1 2/2005 Langer
2005/0070964 A1 3/2005 Hansen et al.
2006/0122648 A1 6/2006 Elghazzawi et al.
2006/0129190 A1 6/2006 Sullivan et al.
2006/0129191 A1 6/2006 Sullivan et al.
2006/0136000 A1 6/2006 Bowers
2006/0155336 A1 7/2006 Heath
2006/0173498 A1 8/2006 Banville et al.
2006/0173499 A1 8/2006 Hampton et al.
2006/0173500 A1 8/2006 Walker et al.
2006/0173501 A1 8/2006 Stickney et al.
2006/0206152 A1 9/2006 Covey et al.
2006/0229679 A1 10/2006 Joo
2006/0259080 A1 11/2006 Vaisnys et al.
2007/0179539 A1 8/2007 Degroot et al.
2007/0219588 A1 9/2007 Freeman
2007/0233197 A1 10/2007 Jung et al.
2008/0009908 A1 1/2008 Parascandola et al.
2008/0015645 A1 1/2008 Kelly et al.
2008/0033494 A1 2/2008 Swerdlow
2008/0033495 A1 2/2008 Kumar
2008/0046015 A1 2/2008 Freeman et al.

FOREIGN PATENT DOCUMENTS

GB 2314648 1/1998
WO 97/24062 7/1997
WO 98/30282 7/1998
WO 99/24114 5/1999
WO 99/25306 5/1999
WO 02/15836 2/2002
WO 2004/054656 7/2004

OTHER PUBLICATIONS

Aase et al., "CPR Artifact Removal from Human ECG Using Optimal Multichannel Filtering", IEEE Transactions on Biomedical Engineering, vol. 47:11, pp. 1440-1449 (2000).

Afonso et al., "Detecting Ventricular Fibrillation", IEEE Engineering in Medicine and Biology, vol. 14:2, pp. 152-159 (1995).

Al-Fahoum et al., "Combined wavelet transformation and radial basis neural networks for classifying life-threatening cardiac arrhythmias", Medical & Biological Engineering & Computing, vol. 37:5, pp. 566-573 (1999).

Amann et al., Reliability of Fibrillation Detection Algorithms In Automatic External Defibrillators (AEDs), Dept. of Anaesthesia and Intensive Care Medicine, Leopold-Franzens-Universitat Innsbruck, Anichstr. 35, A-6020 Innsbruck, Austria, Dept. of Computer Science, Applied Mathematics Group, FH-Vorarlberg, Achstr. 1, A-6850 Dombirn, Austria. At the top of the paper I have is the following: Jahrestaguug der Osterreichischen Deutschen und Schweizerischen Gesellschaft fur Biomedizimische Technik Sep. 2003.

American Red Cross—Adult CPR/AED Training—Workplace Programs, http://www.redcross.org/hss/cpraed.html, printed from Internet May 14, 1999.

Barro et al., "Algorithmic sequential decision-making in the frequency domain for life threatening ventricular arrhythmias and imitative artifacts: a diagnostic system", J. Biomed. Eng., vol. 11:4, pp. 320-328 (1989).

Botsivaly et al., "Evaluation of a new technique for the Detection of Ventricular Fibrillation and Ventricular Tachycardia", Procs of the 22nd Ann EMBS Int Conf, Chicago, IL (2000).

Callaway et al., "Scaling exponent predicts defibrillation success for out-of-hospital ventricular fibrillation cardiac arrest," Circulation 103(12):1656-1661 (2001).

Callaway et al., "Ventricular Fibrillation Waveform Predicts Defibrillation Success by Automatic External Defibrillators", Academic Emergency Medicine, vol. 7:5, pp. 1-2 (2000).

Cardiac Science Brochure, Analysis Algorithm Overview, Powerheart® AED Automated External Defibrillator with RHYTHMx® Technology (no date).

Clayton et al., "Comparison of four techniques for recognition of ventricular fibrillation from the surface ECG", Medical & Biological Engineering & Computing, vol. 31:2, pp. 111-117 (1993).
Eftestol et al., "Effects of Interrupting Precordial Compressions on the Calculated Probability of Defibrillation Success During Out-of-Hospital Cardiac Arrest," Circulation, 105, 2270-2273, (2002).
Eftestøl et al., "Predicting Outcome of Defibrillation by Spectral Characterization and Nonparametric Classification of Ventricular Fibrillation in Patients With Out-of-Hospital Cardiac Arrest", Circulation, 102:1523-1529 (2000).
Efestol et al., "Probability of successful defibrillation as a monitor during CPR in out-of-hospital cardiac arrested patients," Resuscitation 48(3):245-254 (2001).
Fitzgibbon et al., "Determination of the noise source in the electrocardiogram during cardiopulmonary resuscitation", Crit Care Med, vol. 30:4, pp. S148-S152 (2002).
Flewelling, Nellcor Incorporated, Noninvasive Optical Monitoring, Chap. 88, pp. 1346-1353. CRC Press, Inc., 1995.
Force Sensing Resistors—An Overview of the Technology, FSR Integration Guide & Evaluation Parts Catalog with Suggested Electrical Interfaces (no date).
Ge et al., "Cardiac arrhythmia classification using autoregressive modeling", Biomed Eng. Online, pp. 13, (2002).
Geheb, Frederick J., "A System for the Determination of Ventricular Tachycardia or Ventricular Fibrillation during Cardio-Pulmonary Resuscitation", 2 pages (Apr. 2002).
Gruben et al., "System for Mechanical Measurements During Cardiopulmonary Resuscitation in Humans," IEEE Transactions on Biomedical Engineering, vol. 37, No. 2, Feb. 1990.
Haykin, Adaptive Filter Theory, Third Edition, Upper Saddle River, NJ, USA. Prentice-Hall, 1996.
Heartstream—The Background Behind Our Technology, http://www.heartstream.com/techbk.htm, printed from Internet Jun. 25, 1999.
Husoy et al., "Removal of Cardiopulmonary Resuscitation Artifacts From Human ECG Using an Efficient Matching Pursuit-Like Algorithm", IEEE Transactions on Biomedical Engineering, vol. 49:11, pp. 1287-1298 (2002).
Khadra et al., "Detection of life-threatening cardiac arrhythmias using the wavelet transformation", Medical & Biological Engineering & Computing, vol. 35:5, pp. 626-632 (1997).
Kuo et al., "Computer Detection of Ventricular Fibrillation", Computers in Cardiology, pp. 347-349 (Sep. 1978).
Langhelle et al. "Reducing CPR Artifacts in Ventricular Fibrillation in Vitro," Resuscitation. Mar; 48(3):279-91 (2001).
Lightfoot et al., "Dynamic nature of electrocardiographic waveform predicts rescue shock outcome in porcine ventricular fibrillation," Ann. Emerg. Med. 42(2):230-41 (Aug. 2003).
Menegazzi et al., "Immediate defibrillation versus interventions first in a swine model of prolonged ventricular fibrillation", Resuscitation, vol. 59, pp. 261-270 (2003).
Menegazzi et al., "Ventricular Fibrillation Scaling Exponent Can Guide Timing of Defibrillation and Other Therapies", Circulation, 109:926-931 (Feb. 2004).
Nygards et al., "Recognition of Ventricular Fibrillation Utilizing The Power Spectrum of The ECG", Computers in Cardiology, pp. 393-397 (1997).
Povoas et al., "Predicting the success of defibrillation by electrocardiographic analysis," Resuscitation 53(1):77-82 (2002).
Sherman et al., "Ventricular fibrillation exhibits dynamical properties and self-similarity", Resuscitation, vol. 47, pp. 163-173 (2000).
U.S. Appl. No. 10/421,652 (Marcovecchio, Optical Pulse Sensor for External Defibrillator).
Wang et al., "Effects of Biphasic vs Monophasic Defibrillation on the Scaling Exponent in a Swine Model of Prolonged Ventricular Fibrillation", Academic Emergency Medicine, vol. 8:8, pp. 771-780 (2001).
Watson et al., "A novel wavelet transform based analysis reveals hidden structure in ventricular fibrillation", Resuscitation, vol. 43:2, pp. 121-127 (2000).
Yoji et al., "Adverse effects of interrupting precordial compression during cardiopulmonary resuscitation", Critical Care Medicine, vol. 25:5, pp. 733-736 (1997).
Yu et al., "Adverse Outcomes of Interrupted Precordial Compression During Automated Defibrillation", Circulation, pp. 368-372 (Jul. 2002).
Noc et al., "Electrocardiographic Prediction of the Success of Cardiac Resuscitation," Critical Care Medicine, Williams and Wilkins Company, Baltimore, MA, US, vol. 27, No. 4, pp. 708-714(Apr. 1, 1999).

* cited by examiner time magnitude time magnitude

AUTOMATIC THERAPY ADVISOR

TECHNICAL FIELD

This invention relates to techniques for automatically advising as to the appropriate therapy for a patient, e.g., the particular therapy to be used for cardiac resuscitation.

BACKGROUND

The heart relies on an organized sequence of electrical impulses in order to beat effectively. Any deviation from this normal sequence is known as "arrhythmia." A class of devices includes signal processing software that analyzes electrocardiography (ECG) signals acquired from the victim to determine when a cardiac arrhythmia such as ventricular fibrillation (VF) or shockable ventricular tachycardia (VT) exists. These devices include automated external defibrillators (AEDs), ECG rhythm classifiers, or ventricular arrhythmia detectors. An AED is a device that literally "talks" the provider through a process of evaluating a patient for, attaching the patient to, and activating, the AED therapy. This device is capable of recognizing the two distinct cardiac waveforms: VT and VF.

VT is a tachydysrhythmia originating from a ventricular ectopic focus, characterized by a rate typically greater than 120 beats per minute and wide QRS complexes. VT may be monomorphic (typically regular rhythm originating from a single focus with identical QRS complexes) or polymorphic (unstable, may be irregular rhythm, with varying QRS complexes). An example rhythm for an unstable VT is illustrated in FIG. 1A. Depending on the rate and the length of time that the VT has been sustained, a heart in the VT state may or may not produce a pulse (i.e., pulsatile movement of blood through the circulatory system). The cardiac activity still has some sense of organization (note that the "loops" are all basically the same size and shape). If there is no pulse associated with this VT rhythm, then the VT is considered to be unstable and a life threatening condition. An unstable VT can be treated with an electrical shock or defibrillation.

Supraventricular tachycardia (SVT) is a rapid heartbeat that begins above the hearts lower chambers (the ventricles). SVT is an abnormally fast heart rhythm that begins in one of the upper chambers of the heart (atria), a component of the heart's electrical conduction system called the atrioventricular (AV) node, or both. Although SVT is rarely life-threatening, the symptoms which include a feeling of a racing heart, fluttering or pounding in the chest or extra heartbeats (palpitations), or dizziness can be uncomfortable.

VF is usually an immediate life threat. VF is a pulseless arrhythmia with irregular and chaotic electrical activity and ventricular contraction in which the heart immediately loses its ability to function as a pump. VF is the primary cause of sudden cardiac death (SCD). An example rhythm for VF is illustrated in FIG. 1B. This waveform does not have a pulse associated with it. There is no organization to this rhythm (note the irregular size and shape of the loops.) The pumping part of the heart is quivering like a bag of worms, and it is highly unlikely that this activity will move any blood. The corrective action for this rhythm is to defibrillate the heart using an electrical charge.

A normal heart beat wave starts at the sinoatrial node (SA node) and progresses toward the far lower corner of the left ventricle.

A massive electrical shock to the heart can correct the VF and unstable VT rhythms. This massive electrical shock can force all the cardiac cells in the heart to depolarize at the same time. Subsequently, all of the cardiac cells go into a short resting period. The hope is that the sinoatrial node (SA node) will recover from this shock before any of the other cells, and that the resulting rhythm will be a pulse producing rhythm if not normal sinus rhythm.

For AEDs, algorithms to recognize the two waveforms VT and VF are designed to perform ECG analyses at specific times during a rescue event of a patient using defibrillation and cardio-pulmonary resuscitation (CPR). The first ECG analysis is usually initiated within a few seconds following attachment of the defibrillation electrodes to the patient. Subsequent ECG analyses may or may not be initiated based upon the results of the first analysis. Typically, if the first analysis detects a shockable rhythm, the rescuer is advised to deliver a defibrillation shock. Following the shock delivery, a second analysis is automatically initiated to determine whether the defibrillation treatment was successful or not (i.e., the shockable ECG rhythm has been converted to a normal or other non-shockable rhythm). If this second analysis detects the continuing presence of a shockable arrhythmia, the AED advises the user to deliver a second defibrillation treatment. A third ECG analysis may then be initiated to determine whether the second shock was or was not effective. If a shockable rhythm persists, the rescuer is then advised to deliver a third defibrillation treatment.

Following the third defibrillator shock or when any of the analyses described above detects a non-shockable rhythm, treatment protocols recommended by the American Heart Association and European Resuscitation Council require the rescuer to check the patient's pulse or to evaluate the patient for signs of circulation. If no pulse or signs of circulation are present, the rescuer is trained to perform CPR on the victim for a period of one or more minutes. The CPR includes rescue breathing and chest compressions. Following this period of CPR, the AED reinitiates a series of up to three additional ECG analyses interspersed with appropriate defibrillation treatments as described above. The sequence of three ECG analyses/defibrillation shocks followed by 1-3 minutes of CPR, continues in a repetitive fashion for as long as the AED's power is turned on and the patient is connected to the AED device. Typically, the AED provides audio prompts to inform the rescuer when analyses are about to begin, what the analysis results were, and when to start and stop the delivery of CPR.

One limitation associated with many AEDs is that current automated ECG rhythm analysis methods cannot function with extra noise due to CPR chest compressions. Thus, conventional practice is to interrupt chest compressions while performing ECG rhythm analysis. Long interruptions of chest compressions have been shown to result in higher failure rate of resuscitation. Many studies have reported that the discontinuation of precordial compression can significantly reduce the recovery rate of spontaneous circulation and 24-hour survival rate. These studies include "Adverse effects of interrupting precordial compression during cardiopulmonary resuscitation" by Sato et al (Critical Care Medicine, Volume 25(5), May 1997, pp 733-736), "Adverse Outcomes of Interrupted Precordial Compression During Automated Defibrillation" by Yu et al. (Circulation, 2002), and"Predicting Outcome of Defibrillation by Spectral Characterization and Nonparametric Classification of Ventricular Fibrillation in Patients With Out-of-Hospital Cardiac Arrest" by Eftestøl et al. (Circulation, 2002). Thus, it is useful to recognize abnormal heart rhythms during chest compressions.

There is recent clinical evidence showing that performing chest compressions prior to defibrillation under some circumstances can be beneficial. Specifically, it is clinically beneficial to treat a patient with chest compressions prior to defibrillation if the response times of the medical emergency system result in a delay of more than four minutes such that the patient is in cardiac arrest for more than four minutes. If the response times of the medical emergency system result in a capability to treat the patient in sooner than a four minute delay, it can be better for the patient to be treated with defibrillation first. Methods have been developed to determine from the ECG waveform both whether the patient has been in cardiac arrest for longer than the 4 minutes as well as time independent measures of when the most optimal time is to shock. "Non-invasive monitoring and treatment of subjects in cardiac arrest using ECG parameters predictive of outcome" by Brown and Dzwonczyk (U.S. Pat. No. 5,683,424) describes methods to determine from the ECG waveform whether the patient has been in cardiac arrest for longer than the 4 minutes. "Method and system for predicting the immediate success of a defibrillatory shock during cardiac arrest" (U.S. Pat. No. 6,171,257 by Weil et al.) and "Ventricular Fibrillation Scaling Exponent Can Guide Timing of Defibrillation and Other Therapies" by Menegazzi et al. (2004 American Heart Association, Inc.) describe time independent measures of when the most optimal time is to shock. These algorithms use spectral analysis of the ECG to predict defibrillation shock success in some manner. Current methods utilizing spectral analysis of the ECG for chest compression artifact rejection, defibrillation success prediction, and therapeutic decision-making typically specify a set of parameters in the ECG frequency spectrum to be detected. For example, U.S. Pat. No. 5,683,424 compares a centroid or a median frequency or a peak power frequency from a calculated frequency spectrum of the ECG to thresholds to determine if a defibrillating shock is necessary. These parameters do not uniquely specify the frequency or time domain characteristics. For example, the median frequency of the ECG spectrum for almost all patients in ventricular fibrillation decreases initially then increases again after several minutes, making it difficult to use median frequency to predict how long a patient has been in cardiac arrest. Thus, the patient can have the same median frequency at widely differing durations of cardiac arrest. Using amplitudes of the frequency spectrum of the ECG can be limited because the amplitudes are dependent on both the cardiac electrical output as well as position of the ECG lead electrodes on the patient.

Some conventional automated ECG rhythm analysis methods detect VF and other arrhythmic heart rhythms by using spectral analysis of the ECG signals with the assumption that the difference in the power spectrum between ECGs of normal heart rhythms and abnormal rhythms is such that during the abnormal rhythm the ECG is concentrated or mainly sinusoidal in a narrow band of frequencies between 4 and 7 Hz, while in normal rhythm the ECG is a broadband signal with major harmonics up to at least 25 Hz. For example, "Comparison of four techniques for recognition of ventricular fibrillation from the surface" by Clayton et al. (ECG Medical & Biological Engineering & Computing 1993; 31:111-117) and "Algorithmic sequential decision-making in the frequency domain for life threatening ventricular arrhythmias and imitative artifacts: a diagnostic system" by Barro et al. (Journal of Biomedical Engineering, 1989, Volume 11) analyze the frequency domain of the ECG to check if the ECG is mainly sinusoidal in the narrow band of frequencies. One problem with these conventional methods is that CPR changes the assumption behind the methods so that VF and other dangerous rhythms cannot be typically detected during chest compressions.

Adaptive filters have been used in many studies to remove the artifact due to CPR chest compression from the ECG signal. These studies include "CPR Artifact Removal from Human ECG Using Optimal Multichannel Filtering" by Aase et al. (IEEE Transactions on Biomedical Engineering, Vol. 47, No. 11, November 2000), "Removal of Cardiopulmonary Resuscitation Artifacts From Human ECG Using an Efficient Matching Pursuit-Like Algorithm" by Husøy et al. (IEEE Transactions on Biomedical Engineering, Vol. 49, No. 11, November 2002), "and U.S. Pat. No. 6,390,996 by Halperin et al (2002). The adaptive filters use compression depth and thoracic impedance as reference signals to estimate the artifacts in the ECG signal. The adaptive filter's parameters are updated by calculating the inverse of a cross-correlation matrix or the auto- and cross-spectra of the signal. The artifacts could be reduced when these adaptive filters were applied. However, there is usually a significant part of the artifact left in the estimated ECG signal. Moreover, the adaptive-filter algorithm sometimes has a high computational complexity.

These adaptive filtering methods use the compression depth as the reference signal to remove the chest compression artifact from the ECG signals. This is based on the assumption that the chest compression artifact is correlated with the reference signal (compression depth) and independent of the desired ECG signal. This can be true for an infinitely long ECG signal but the estimated coefficients can be biased if a limited length of the ECG signal is applied. It is also possible that the reference signals (such as the compression depth) can provide only part of the information about the CPR artifact presented in the ECG signal, i.e. the noise-reduction ability of the adaptive filter is limited by its knowledge of the noise. Fitzgibbon et al. in "Determination of the noise source in the electrocardiogram during cardiopulmonary resuscitation" (Critical Care Medicine 2002 Vol. 30, No. 4) reported that the thoracic impedance variation due to ventilation or chest compression has little correlation with the artifact in ECG recording during chest compressions. Fitzgibbon et al. (2002) further suggested that the source of the noise in the signal during chest compressions is the electrode motion and related to the electrode's electrical properties, which makes the relation between the noise and the compression depth more complicated. Thus, the artifact cannot be sufficiently attenuated for satisfactory results with the conventional advisory algorithm for fibrillation detection.

One method for evaluating medical tests is to determine a test's ability to correctly detect disease, also known as sensitivity, and the test's ability to avoid labeling normal things as disease, also known as specificity. Ideally, a medical test has 100% sensitivity and 100% specificity. When a medical test is imperfect, sensitivity and specificity are plotted on a graph called a receiver-operator characteristics (ROC) curve. Variables in the medical test can be chosen such that the resulting point of the medical test on the ROC curve is closest to a point with 100% sensitivity and 100% specificity.

SUMMARY

In general, the invention features a method of automatically determining which type of treatment is most appropriate for (or the physiological state of) a patient. The method comprises transforming one or more time domain measurements from the patient into frequency domain data representative of the frequency content of the time domain measurements; processing the frequency domain data to form a plurality of spectral bands, the content of a spectral band representing the frequency content of the measurements within a frequency band; forming a weighted sum of the content of the spectral bands, with different weighting coefficients applied to at least some of the spectral bands; determining the type of treatment (or physiological state) based on the weighted sum.

In preferred implementations, one or more of the following features may be incorporated. The weighting coefficients may be ones chosen using a regression analysis comparing actual time domain measurements and actual outcome of therapy for a population of patients. The weighting coefficients may have been chosen to improve a correlation between the weighted sum and the outcome of therapy. The weighting coefficients are different for at least two different therapy stages. The therapy may be cardiac resuscitation, and the measurement comprises ECG signals. The measurement may comprise ECG signals, and the therapy stages may comprise at least arrival at patient's side, pre-shock, and post-shock. The therapy stage may be based at least in part on rescuer entered data indicative of the stage of therapy. The therapy stage may be based at least in part on rescuer entered data indicative of at least what drugs have been delivered to the patient. The rescuer entered data may be further indicative of whether the patient has been intubated, and whether an automatic external chest compressor has been used. The determining may comprise comparing the weighted sum to a threshold. The threshold may be different for at least two therapy stages. When the therapy is cardiac resuscitation, and the measurement comprises ECG signals, if the weighted sum exceeds the threshold the type of treatment determined to be appropriate may be delivery of a defibrillation shock. The threshold used when the therapy stage is arrival at the patient's side may be lower than the threshold used for later therapy stages.

In other aspects, the invention features a method of automatically determining which type of treatment is most appropriate for a cardiac arrest victim, the method comprising transforming one or more time domain electrocardiogram (ECG) signals into a frequency domain representation comprising a plurality of discrete frequency bands, combining the discrete frequency bands into a plurality of analysis bands, wherein there are fewer analysis bands than discrete frequency bands, determining the content of the analysis bands, and determining the type of treatment based on the content of the analysis bands.

In preferred implementations, one or more of the following features may be incorporated. Transforming may comprise the Fourier transform. Transforming may comprise a Wavelet transform. Transforming may comprise a Radon transform. Determining the content of the analysis bands may comprise determining a plurality of values. The content and the plurality of values may be calculated at more than two points in time, and wherein the sequence of plurality of values in time may define a trajectory. The trajectory may be analyzed using estimation and prediction methods. The analysis method may involve use of a recursive filter. The recursive filter may be a Kalman filter. The analysis method may involve use of a Particle Filter. The analysis of the trajectory may be used to predict defibrillation success. The analysis of the trajectory may be used to determine whether it is appropriate to defibrillate or deliver an alternative therapy such as chest compressions, drugs such as epinephrine, constitutive nutrients such as glucose, or other electrical therapy such as pacing. A mathematical transformation may be performed on the trajectory. The transformation may be a projection of the trajectory onto a plane within the parameter space. Image mensuration algorithms may be employed to evaluate the features of the two dimensional projection of the trajectory. The content may comprise at least two parameters descriptive of the content of an analysis band from the analysis bands. Determining the content of an analysis band may comprise quantifying the energy within an analysis band. Quantifying the energy within an analysis band may comprise determining at least one number characterizing the energy of the highest peak within the band. Quantifying the energy with an analysis band may comprise determining an overall or average energy for the band. The invention further comprises analyzing the variation over time of the content of the analysis bands. The bands may be about 0.5 Hz in width. The bands may be of unequal widths such that additional resolution is provided for frequency bands that are of greater importance in the analysis. Frequencies less than 3 Hz may be subdivided into bands whose widths are larger than those in the 6-12 Hz frequency range. Each band may be composed of an aggregation of multiple spectral measurements. Characteristics of the distribution of spectral measurements within the band may include at least one of the following descriptors: mean spectral energy, spectral energy variance, median spectral energy, maximum spectral energy, or minimum spectral energy.

In another aspect, the invention features a method of automatically determining which type of treatment is most appropriate for a cardiac arrest victim, the method comprising transforming one or more time domain ECG signals into a frequency domain generally containing a plurality of peaks, processing the frequency domain representation to characterize at least a plurality of the peaks, wherein characterizing a peak comprises determining a plurality of parameters characterizing the peak, and determining the type of treatment based on the parameters characterizing at least some of the peaks.

In preferred implementations, one or more of the following features may be incorporated. The invention may further comprise analyzing the variation over time of at least some of the plurality of parameters characterizing at least some of the plurality of peaks. The content and the plurality of values may be calculated at more than two points in time, and wherein the sequence of plurality of values in time may define a trajectory. The trajectory may be analyzed using estimation and prediction methods. The analysis method may involve use of a recursive filter. The recursive filter may be a Kalman filter. The analysis method may involve use of a Particle filter. The analysis of the trajectory may be used to predict defibrillation success. The analysis of the trajectory may be used to determine whether it is appropriate to defibrillate or deliver an alternative therapy such as chest compressions, drugs such as epinephrine, constitutive nutrients such as glucose, or other electrical therapy such as pacing. A mathematical transformation may be performed on the trajectory. The transformation may be a projection of the trajectory onto a plane within the parameter space. Image mensuration algorithms may be employed to evaluate the features of the two dimensional projection of the trajectory. Analyzing the variation over time may comprise determining variation in the frequency of a peak. Determining a plurality of parameters characterizing the peak may comprise estimating a shape of the peak. Estimating a shape of the peak may comprise using a non-linear curve fitting routine. The plurality of the peaks may comprise a largest amplitude frequency peak and peaks having a fraction of an amplitude of the largest amplitude frequency peak. The parameters may comprise a frequency of a peak, an amplitude of the peak, and a width of the peak. The parameters may comprise a depth of the peak. The parameters may comprise a variance of the peak. The parameters may comprise a first moment of the peak. The invention further comprises determining a reference frequency from the frequency domain and determining a variance of the energy of the frequency domain using the reference frequency. The invention may also further comprise determining that the victim is in a sinus arrhythmic state if the variance of the energy of the frequency representation is below a threshold. The reference frequency is one of a mean frequency, a median frequency, a center frequency, and a peak frequency. Determining the type of treatment may comprise determining that the type of treatment is to defibrillate the victim's heart if the following conditions are met: the victim is determined to be in the sinus arrhythmic state, a frequency of a largest amplitude frequency peak is less than a first threshold, and the number of peaks is less than a second threshold. Determining the type of treatment may comprise determining that the type of treatment is chest compressions to the victim if the following conditions are met: the victim is determined to be in the sinus arrhythmic state and a frequency of a largest amplitude frequency peak is greater than a first threshold and if the number of peaks is less than a second threshold. Determining the type of treatment may comprise determining that the type of treatment is monitoring the victim or drug therapy if the following conditions are met: the victim is determined to be in the sinus arrhythmic state, and the number of peaks is greater than a threshold. Determining parameters may comprise measuring a change of one or more parameters of the peaks in a range of the frequency spectrum over multiple digital time samples. Each peak may be considered to retain an identity over the multiple digital time samples if its amplitude and frequency do not change more than a threshold from one time sample to a subsequent time sample. Determining the type of treatment may comprise comparing an oscillation cycle rate of the change to a cycle rate band and if the cycle rate is in the band, determining that the type of treatment is to defibrillate the victim's heart. Determining the type of treatment may further comprise determining that a defibrillating shock to the victim's heart is suitable therapy when the oscillation is at or near a maximum. For two or more peaks the change may be a relative decrease, and wherein determining the type of treatment may comprise comparing the relative decrease to a threshold, and if the relative decrease is above the threshold, the type of treatment may be chest compressions and then defibrillation. The one or more parameters may comprise amplitudes of the peaks, the threshold may be about fifteen percent, and the multiple digital time samples may cover at least a ten second interval. For two or more peaks, the change may be a relative increase, the parameters may comprise frequency of the peaks, amplitude of the peaks, or width of the peaks, and wherein determining the type of treatment may comprise comparing the relative increase to a threshold, and if the relative increase is above the threshold, the type of treatment may be defibrillation. For two or more peaks, the change may be a decrease, and the parameters may comprise variance of the frequency of the peaks, and wherein determining the type of treatment may comprise comparing the decrease to a threshold, and if the decrease is below a threshold, the type of treatment may be defibrillation. The range of the frequency spectrum may be six to twelve Hertz. The invention may further comprise communicating the type of treatment to one of a drug infusion device, a portable chest compression device, and a ventilator. The invention may also further comprise displaying an indication of the type of treatment. Displaying an indication of the type of treatment may comprise displaying a value of an estimation of an accuracy of the type.

In another aspect, the invention features a method of automatically determining which type of treatment is most appropriate for a cardiac arrest victim, the method comprising transforming one or more time domain ECG signals into a frequency domain representation, processing the frequency domain representation to characterize the content of the frequency domain representation in a band from about 6 to about 12 Hz, and determining the type of treatment based on the content in the band.

In preferred implementations, one or more of the following features may be incorporated. The invention may further comprise relying on a ventricular fibrillation (VF) or a ventricular tachycardia (VT) advisory algorithm to determine whether the victim is in VF or VT, and wherein determining the type of treatment may comprise determining when to deliver a shock. The content in the band may comprise a quantitative measure representative of approximately the total energy in the band.

In another aspect, the invention features a method of automatically determining which type of treatment is appropriate for a cardiac arrest victim, the method comprising measuring at least one physiological signal, determining at least two parameters related to the at least one physiological signal, the at least two parameters forming a parameter set, repeating the measurement and calculation at more than two points in time to create a sequence of parameter sets, wherein the sequence of parameter sets defines a trajectory, and analyzing the trajectory using estimation and prediction methods that comprise the use of a recursive filter.

In preferred implementations, one or more of the following features may be incorporated. The recursive filter may be a Kalman filter. The analysis method may involve use of a Particle filter. The analysis of the trajectory may be used to predict defibrillation success. The analysis of the trajectory may be used to determine whether it is appropriate to defibrillate or deliver an alternative therapy such as chest compressions, drugs such as epinephrine, constitutive nutrients such as glucose, or other electrical therapy such as pacing. A mathematical transformation may be performed on the trajectory. The transformation may be a projection of the trajectory onto a plane within the parameter space. Image mensuration algorithms may be employed to evaluate the features of the two dimensional projection of the trajectory. The predicted next state of the parameter set may be used to determine the appropriate treatment. The method may be carried out by a device configured to determine an appropriate therapy for a rescuer to perform on the victim. The probability of defibrillation success associated with a plurality of alternative treatments may be shown on the display of the device. The probability of success with a plurality of treatments may be shown on the display as range of numbers. The device may be an AED that notifies the rescuer in the form of an audible or visual alarm indicating that the paramedic should stop doing compressions for a more accurate analysis of the ECG waveform. The device may be an AED that notifies the rescuer in the form of an audible or visual alarm indicating that the paramedic should alter the therapy being delivered.

In another aspect, the invention features an AED capable of automatically determining which type of treatment is appropriate for a cardiac arrest victim, the AED comprising electrical therapy pads configured to deliver electrical therapy to patients, ECG electrodes smaller in diameter than the electrical therapy pads are integrated into the electrical therapy pads, the smaller ECG electrodes are configured to provide at least one additional electrical vector that is approximately orthogonal to the monitoring vector produced by the ECG signal from the therapy electrodes.

In preferred implementations, one or more of the following features may be incorporated. A vector sum of the at least one additional electrical vector and the monitoring vector may provide a trajectory over time that can be used by the AED in determining which type of treatment is appropriate.

These and other implementations may have one or more of the following advantages. The method uses frequency-domain analysis methods for ECG processing/advisory during chest compressions. This method allows ECG analysis without interruption of chest compression and thus significantly reduces the interruption time during chest compressions, leading to an increase in the success rate of resuscitation.

Some implementations allow for the more complete specification of the ECG waveform spectrum for different cardiac states in a mathematically tractable form that provides improved receiver-operator characteristics (ROC) of the detection algorithm, while reducing the performance burden on the processor.

Other features and advantages of the invention will be apparent from the description and drawings, and from the claims.

DETAILED DESCRIPTION

There are a great many different implementations of the invention possible, too many to possibly describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1A:
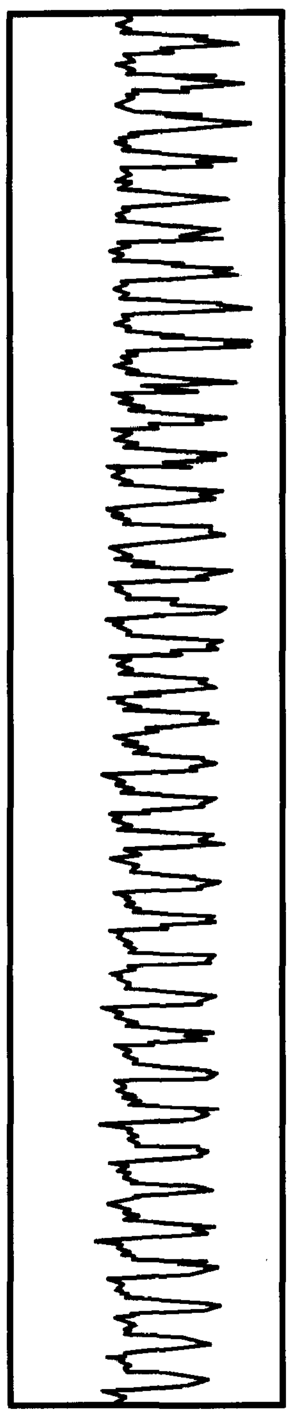
FIG. 1A is a magnitude versus time plot of a ventricular tachycardia (VT) rhythm.
Figure 1B:
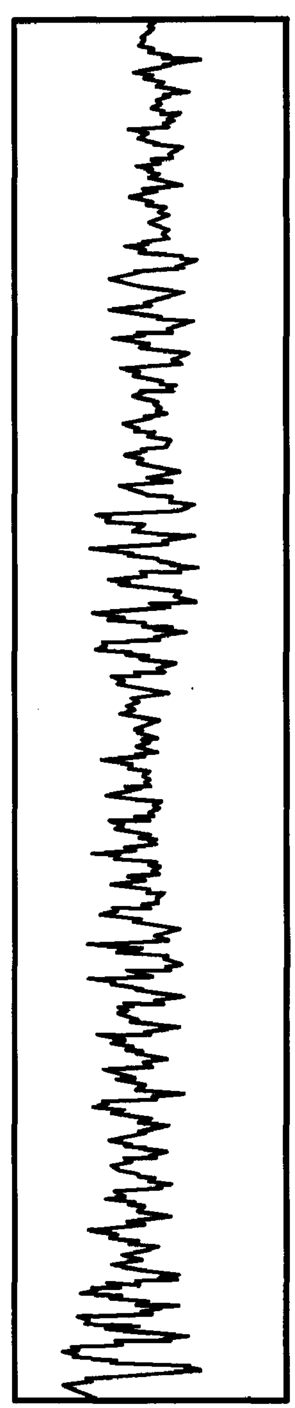
FIG. 1B is a magnitude versus time plot of a ventricular fibrillation (VF) rhythm.
Figures 2, 2A:
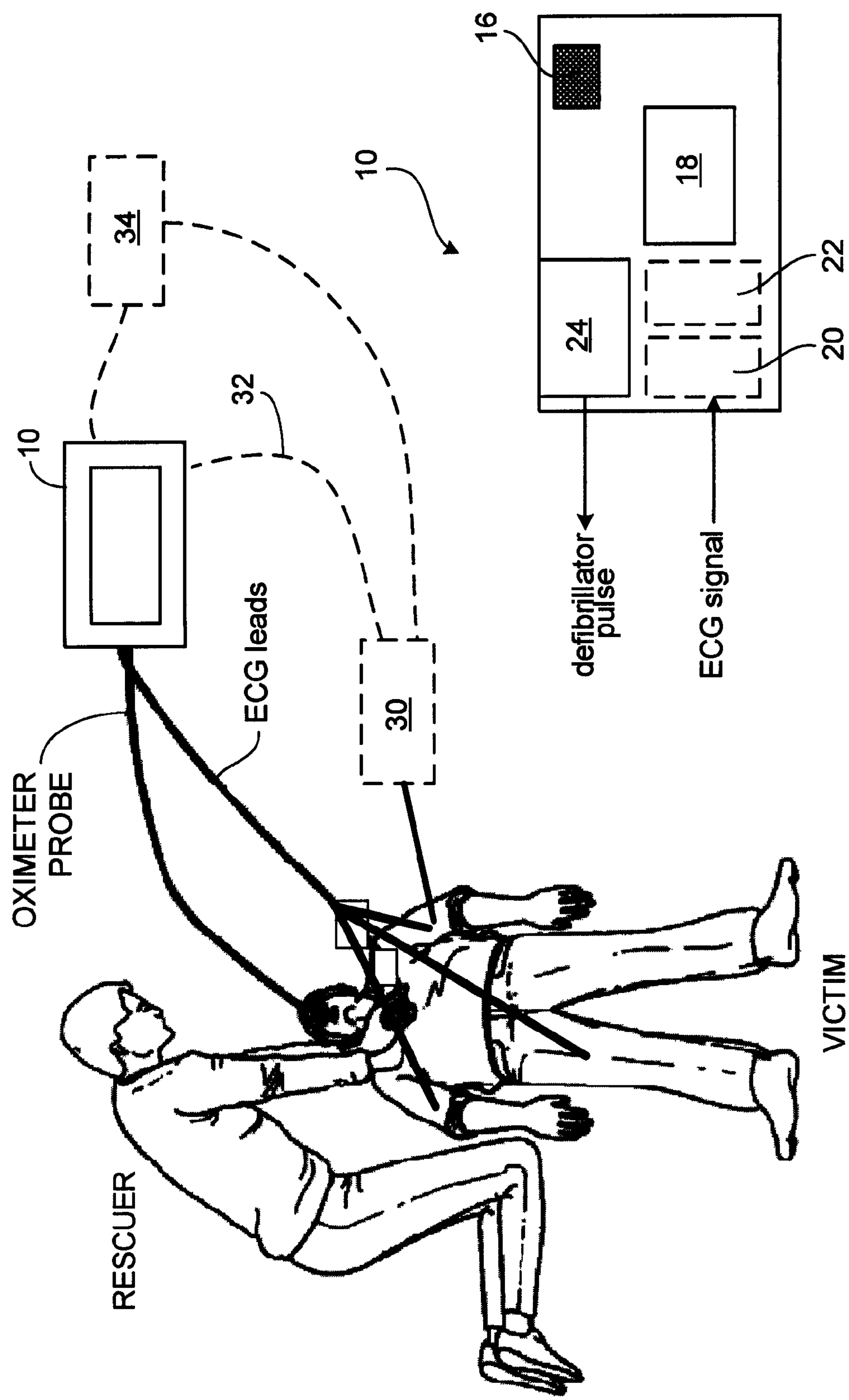
FIG. 2 is a diagram of one implementation including an automatic electronic defibrillator (AED) and a multiple lead electrocardiograph (ECG) device.
FIG. 2A is a diagram of the AED of FIG. 2.

Referring to FIG. 2, a rescuer uses an AED 10 to automatically monitor a victim during cardiac resuscitation. The AED 10 includes a speaker 16, a display screen 18, an analog to digital converter 20, a processor 22, and a defibrillator pulse generator 24. The analog-to-digital converter 20 is connected to a set of ECG leads attached to the victim. The ECG leads monitor the electrical rhythms of the victim's heart. The converter 20 sends the signals from the ECG leads to the processor 22. The processor 22 monitors the victim's heart for dangerous rhythms using the ECG signals while the victim is resuscitated using chest compressions techniques. If the AED 10 detects a dangerous heart rhythm, the AED 10 generates an alarm signal. The alarm signal is noticeable to the rescuer. The AED 10 can generate a defibrillating shock to the victim when the rescuer issues a command to the AED 10. The defibrillating shock is intended to remedy the dangerous rhythm of the victim's heart.

The AED 10 uses a rhythm advisory method for a) quantifying the frequency-domain features of the ECG signals; b) differentiating normal and abnormal ECG rhythms, such as VF; c) detecting the onset of abnormal ECG rhythms; and d) making decisions about the physiological states of the heart. This frequency-domain measure is reliable with or without the presence of the chest compression artifact in the ECG signals. The AED 10, after identifying the current physiological state of the heart, can make a decision about appropriate therapeutic action for the rescuer to make and communicates the action to the rescuer using the speaker 16 and the display screen 18.

This rhythm advisory method can also be incorporated in an ECG rhythm classifier or a ventricular arrhythmia detector.

The AED 10 may incorporate functionality for performing additional therapeutic actions such as chest compressions, ventilations, or delivery of intravenous solution containing metabolic or constitutive nutrients. Based on the results of the analysis of the rhythm advisory method, the AED 10 may automatically deliver the appropriate therapy to the patient. The AED 10 may also be configured in "advisory" mode wherein the AED 10 will prompt the caregiver after the AED 10 has made a determination of the best therapy, and acknowledgement by the caregiver/device operator, in the form of a button press or voice-detected acknowledgement, is required before therapy is delivered to the patient.

The AED 10 then analyzes the ECG signals to predict defibrillation success as well as to decide whether it is appropriate to defibrillate or to deliver an alternative therapy such as chest compressions, drugs such as epinephrine, constitutive nutrients such as glucose, or other electrical therapy such as pacing.

In some examples, one or more therapeutic delivery devices 30 automatically deliver the appropriate therapy to the patient. The therapeutic delivery devices 30 are physically separate from the defibrillator AED 10 and control of the therapeutic delivery devices 30 may be accomplished by a communications link 32. The communications link 32 may take the form of a cable connecting the devices 10, 30, but preferably the link 32 is via a wireless protocol such as Bluetooth or a wireless network protocol such as Institute of Electrical and Electronics Engineers (IEEE) 802.11. Bluetooth is a telecommunications industry specification that describes how mobile computing devices can be interconnected using a short-range wireless connection. The therapeutic delivery device 30 can be a portable chest compression device that is commercially available as the Autopulse™, provided by Revivant of Sunnyvale, Calif. In other examples, the therapeutic delivery device 30 is a drug infusion device that is commercially available as the Power Infuser™, provided by Infusion Dynamics of Plymouth Meeting, Pa., or the Colleague CX™, provided by Baxter Healthcare Corp., of Round Lake, Ill. The therapeutic delivery device 30 can be a ventilator that is commercially available as the iVent™, provided by Versamed of Pearl River, N.Y. The therapeutic delivery device 30 can also include multiple therapies such as defibrillation, chest compression, ventilation and drug infusion.

In other examples, control and coordination for the overall resuscitation event and the delivery of the various therapies may be accomplished by a device 34 or processing element external to the AED 10, for instance the device 34 may download and process the ECG data from the AED 10; analyze the ECG signals, perform the determinations based on the analysis, and control the other therapeutic devices 30, including the AED 10.

In other examples, the AED 10 may perform all the processing of the ECG, including analyzing the ECG signals, and transmit to the control device 34 only the final determination of the appropriate therapy, whereupon the control device 34 would perform the control actions on the other linked devices 30. The control device 34 is commercially available as the Autopulse™, provided by Revivant of Sunnyvale ,Calif.

The chest compression artifact can be separated from the ECG signal components in the frequency domain. This makes it possible for the AED 10 to process the ECG signal without halting the processing during CPR chest compressions. The compression rate during CPR chest compressions recommended by American Heart Association (2000) is 100 per minute or 1.7 Hz and the frequency range used for quantifying the frequency-domain features of the ECG signals can be set to be higher than that (preferably but not limited to be 3 Hz and up) using a high pass frequency filter.

The rhythm advisory method quantifies the energy distribution of the ECG signal in the frequency domain with a quantification method. The quantification result can be used to differentiate normal and dangerous ECG rhythms with or without the presence of the chest compression artifact. In one method, the AED 10 breaks up the frequency domain of the ECG signal into analysis frequency bands. The AED 10 then analyzes the different frequency bands for energy or variation over time to determine an appropriate treatment for the victim. In the preferred embodiment, the bands are 0.5 Hz in width, though they may also be divided into unequal widths such that additional resolution is provided for frequency bands that are of greater importance in the analysis. For instance, frequencies less than 3 Hz may be subdivided into only three equally spaced bands while the range from 3-5 Hz may have 0.5 Hz bands, and the range of 6-12 Hz may have 0.25 Hz bands. Each band may be composed of an aggregation of multiple spectral measurements. For each band, characteristics of the distribution of spectral measurements within the band may include such descriptors, e.g., as mean spectral energy, spectral energy variance, median spectral energy, maximum spectral energy, minimum spectral energy.

In one example of the analysis frequency bands, the AED 10 generates the frequency bands based on peaks in the frequency spectrum. Thus, one frequency band corresponds to the frequency spread of a given peak in the frequency spectrum. There are common algorithms for identifying peaks in the frequency spectrum that include calculating slopes and energy at different points of the frequency spectrum. For each of these peaks, the AED 10 uses a non-linear parameter estimation algorithm or curve fitting algorithm to estimate the shape of the peak. From this spectral shape, the AED 10 calculates parameters about the peak.

The quantification method differentiates various spectral patterns and shapes. The AED 10 makes a decision about the physiological state of the heart and suitable therapy based on the quantification results. The quantification method of the rhythm advisory method is a combination of measures from sub-methods. Some of these sub-methods differentiate various spectral shapes, including but not limited to: (1) the number of peaks in the target frequency range, (2) the relative strength/peak value of various spectral peaks, (3) the relative bandwidth of various spectral peaks and (4) the variance of the energy distributed in a selected frequency range. One or more sub-methods can also measure change in the spectral information over time.

These measures can be combined in a multi-dimension space to enhance both the sensitivity and specificity of the decision. One or more information processing techniques can be used to quantify the combination following the computation of these measures in order to make a decision based on the combination. The information processing techniques can include but are not limited to simple combining rules or math, neural networks, expert systems incorporating fuzzy or standard logic, or other artificial intelligence techniques. The additional measures can also include measurement of velocity or acceleration of chest compression during chest compressions according to the techniques taught by U.S. application Ser. No. 10/704,366, Method and Apparatus for Enhancement of Chest Compressions During Chest Compressions, filed on Nov. 6, 2003.

The information processing techniques include simple combining rules or math, neural networks, expert systems incorporating fuzzy or standard logic, or other artificial intelligence techniques. These techniques make a decision based on the combination of measures about the physiological state of the heart and suitable therapy. The different measures are individual indications that have varying degrees of uncertainty about the physiological state of the heart and suitable therapy. In some examples, the information processing technique is trained automatically using software techniques known to those skilled in this art and a database of ECG rhythms that include outcome data. These examples include neural networks. In other examples, the information processing technique is generated manually based on observations of ECG patterns and outcomes. These examples include simple combining rules or math, and expert systems utilizing fuzzy or standard logic. In the example of expert systems utilizing standard logic, a programmer manually generates logical rules without uncertainty, the rules specifying preconditions such as "if measure A recommends defibrillation" and "if measure B recommends defibrillation", and if these preconditions are met, the AED 10 automatically defibrillates the patient. In the example of expert systems utilizing fuzzy logic, the rules are more "fuzzy" and the states to be combined incorporate some degree of uncertainty based on human language. For instance, the fuzzy logic rules can incorporate such input as "measure A detects a strong need for defibrillation" versus "measure A detects a weak need for defibrillation". The fuzzy logic framework combines the different measures and outputs results such as "strong need for defibrillation" or "weak need for defibrillation".

The method of making the decision about the physiological state is to choose from a group of possible states, each of which corresponds to a predetermined value range of the proposed measure. The possible states can include but are not limited to normal sinus rhythm, VF, shockable (unstable) VT, stable VT, supraventricular rhythm, and pulseless electrical activity.

Figure 3A:
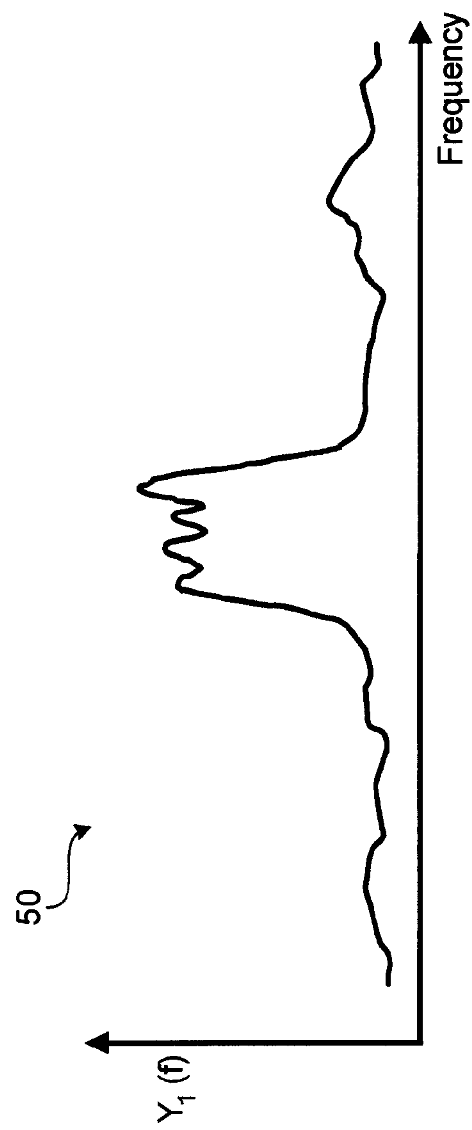
FIG. 3A is an example of a frequency spectrum plot with the energy concentrated within a small frequency range.
Figure 3B:
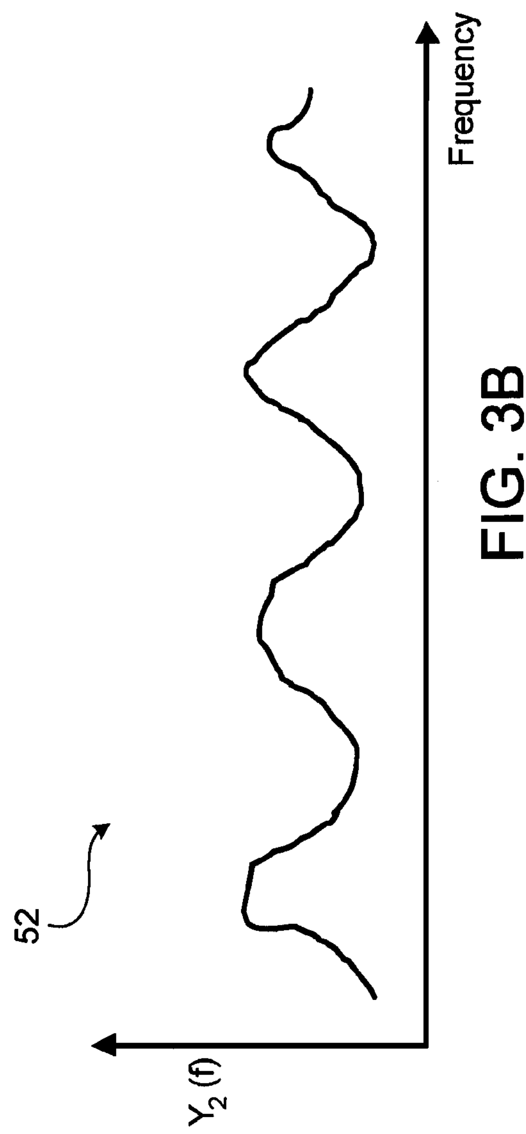
FIG. 3B is an example of a frequency spectrum plot with the energy distributed over a relatively larger frequency range.

One possible sub-method for the quantification method is the variance of the energy distributed in a selected frequency range, or variance sub-method. Two examples of energy-distribution patterns are shown in FIGS. 3A and 3B. The frequency spectrum plots of FIGS. 3A and 3B are calculated using a fast Fourier transform (FFT) of a signal over time. Referring to FIG. 3A, the energy $Y_1(f)$ of a frequency spectrum 50 is concentrated within a narrow frequency band and represents a pattern found in an arrhythmic state such as VF. Referring to FIG. 3B, the energy $Y_2(f)$ of a frequency spectrum 52 is distributed over a wide frequency range and represents a pattern found in a non-dangerous heart rhythm or normal sinus rhythm. The variance sub-method quantifies the features of the two frequency spectra 50, 52 and thus the variance sub-method can differentiate between an arrhythmic state and normal sinus rhythm.

One example of the variance sub-method calculates the variance of the energy from a reference frequency ($F_{ref}$) of the spectrum. Possible candidates of the reference frequency include but are not limited to the mean frequency, the median frequency, the center frequency, or the peak frequency of the spectrum.

In this example, the variance sub-method computes the weighted distance of each frequency component from the reference frequency of the spectrum and thus quantifies the energy-distribution pattern. An example of this measure, the energy-frequency variance (EFV) can be calculated with the following mathematical equation:

$$EFV = \frac{\int (f - F_{ref})^2 \times Y(f) df}{\int Y(f) df}$$

However, the variance sub-method is not limited to this mathematical equation. Measures that quantify the weighted or un-weighted distance of the frequency components from a reference frequency of the frequency spectrum can be used for this measure.

Referring to FIG. 3A, energy of the spectrum 50 is concentrated within a narrow frequency range and thus the spectrum has a relatively small EFV value. Referring to FIG. 3B, energy of the spectrum 52 is distributed over a relatively wider frequency range and the spectrum has a relatively larger EFV value. Thus, the EFV value can be used to distinguish between a normal sinus rhythm and an arrhythmic sinus rhythm (e.g., VF).

Figure 4:
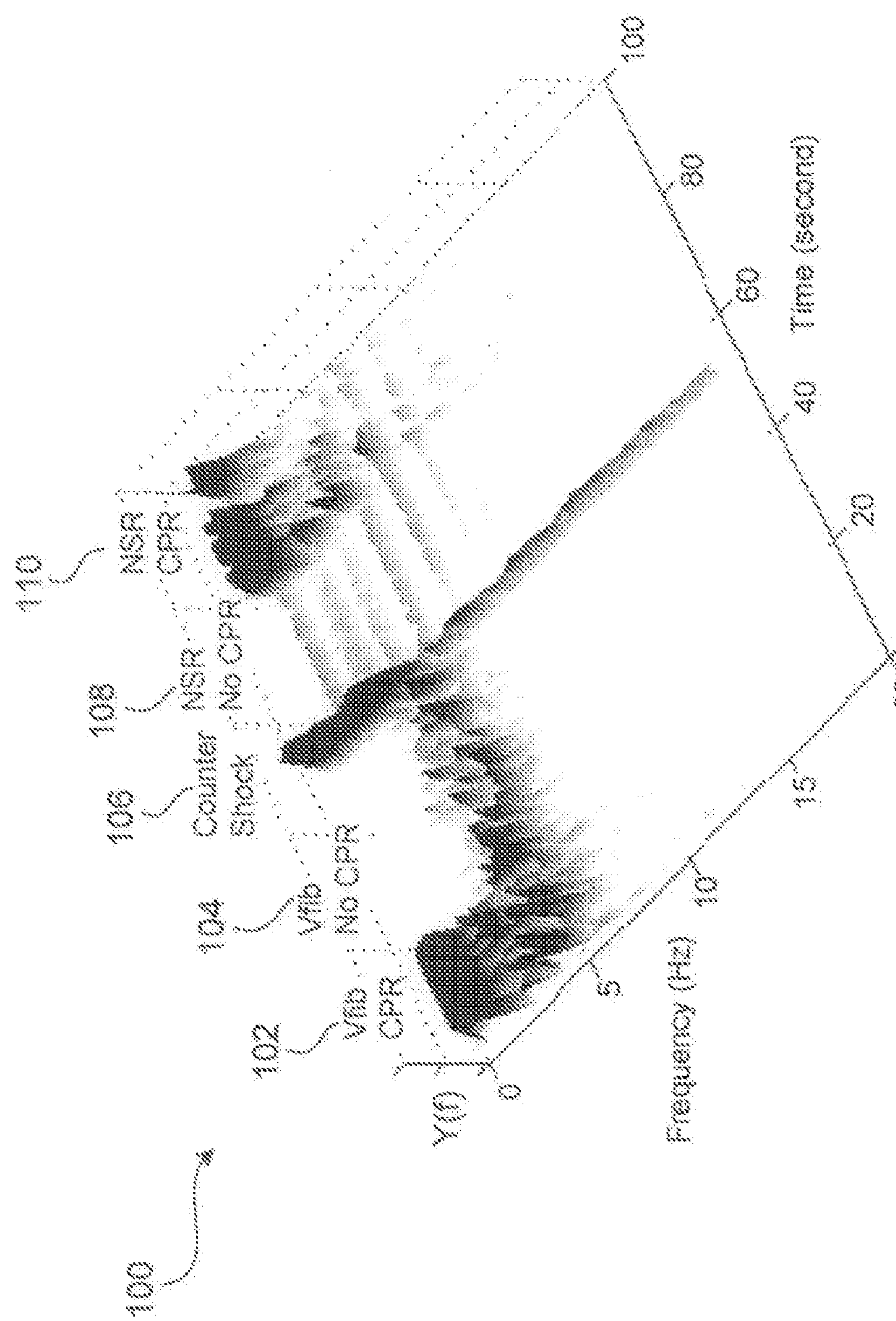
FIG. 4 is an example of an ECG spectrum as a function of time. The magnitude (or energy) of the spectrum is encoded by the grayscale. A darker color corresponds to a higher magnitude.

Referring to FIG. 4, a spectrum 100 of a piece of an ECG signal is a function of time. Part 102 of the signal shows a VF rhythm during chest compressions. Part 104 of the signal shows a VF rhythm without chest compressions. The VF is terminated by an electrical shock 106, which is followed by a period of normal sinus rhythm (NSR). During this NSR period, part 108 has no chest compressions while part 110 has chest compressions. Chest compression artifacts that are characterized by strong low-frequency (below 3 Hz) components can be observed in the first 15 seconds (part 102) and the last 10 seconds (part 110) of this time-frequency plot 100. During the time periods 102 and 104 that are associated with VF (i.e. before the electrical shock 106), the energy distribution Y(f) above 4 Hz is clearly concentrated in a small frequency range, with or without the presence of the chest compression artifact. During the time periods 108 and 110 of NSR (i.e. after the electrical shock 106), the energy distribution Y(f) above 4 Hz has a pattern that the energy is distributed over a wide frequency range, with or without the presence of the chest compression artifact.

Figure 5:
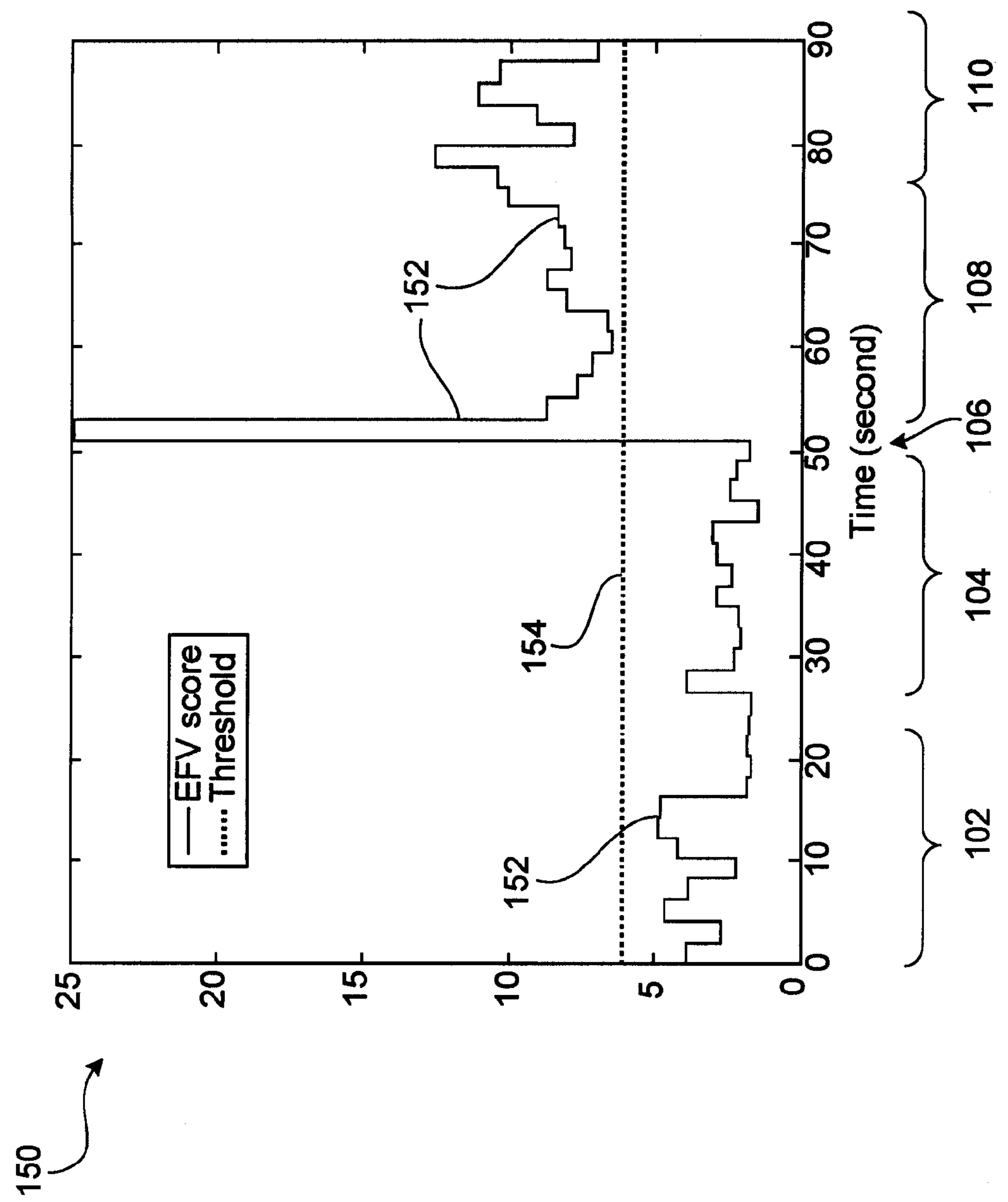
FIG. 5 is an EFV score of the signal in FIG. 4 as a function of time.

Referring to FIG. 5, an EFV score 152 is calculated from the signal 100 (shown in FIG. 4). A threshold 154 can be used to distinguish an arrhythmic rhythm from a normal sinus rhythm. Thus, during the first 50 seconds (parts 102 and 104 having VF rhythm) of the signal 100, the EFV score 152 is below the threshold 154.

Figure 6:
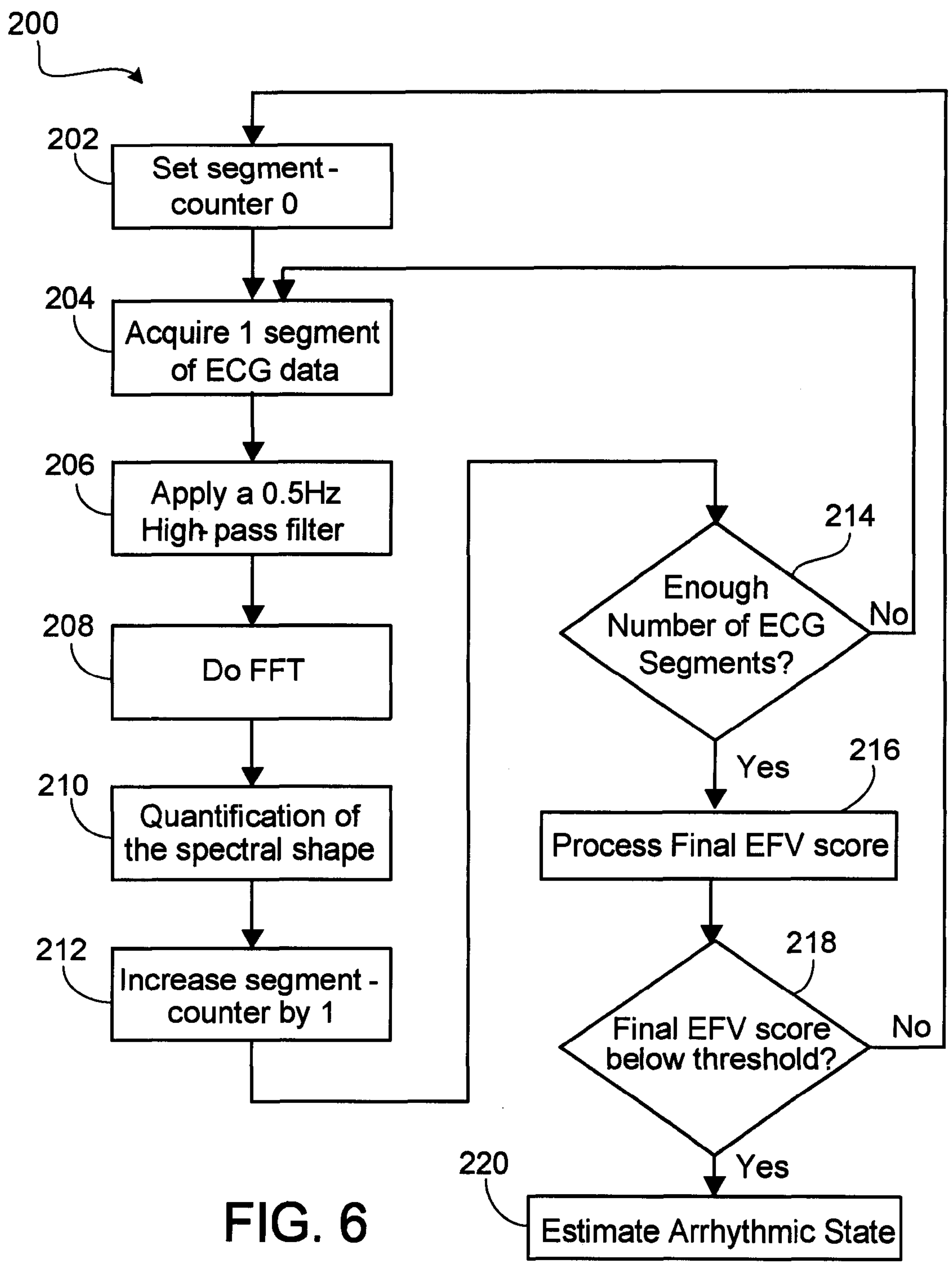
FIG. 6 is a flow chart of a process for detecting VF in a patient during chest compressions.

Referring to FIG. 6, a variance sub-method 200 is implemented in the software and/or hardware of the AED 10. The ECG data acquired by the front-end analog to digital converter 10 of the AED 10 is processed in a segment-by-segment manner. The number of segments to be processed before a decision is made is predetermined (e.g., 9 segments).

The length of a segment is preferably 2 seconds and each segment preferably has a 1-second overlap with both the segment before and after itself, for the desired frequency and time-domain resolution.

The segment-counter is set (202) to be zero when the processing starts and the first segment of the signal is acquired (204). A high-pass filter with a desired cutoff frequency (preferably but not limited to be 0.5 Hz) is then applied (206) to remove the baseline drift. The frequency-domain representation of the filtered signal is acquired via a fast fourier transform (FFT) (208). The spectral shape is quantified (210) using a preferred method. In an example, the EFV score is calculated based on this frequency-domain representation and the frequency range for the EFV calculation is selected such that the low-frequency part where the chest compression artifact dominates is excluded.

The segment counter is increased (212) by one after the quantification of the spectral shape. If (214) all of the predetermined number of segments have been processed, the quantification results are processed (216) to get a final score (including but not limited to the mean value of the EFV scores), otherwise the next segment of ECG signal is processed. In some implementations, the final score is an average of the scores from the segments.

An estimate of the physiological state of the heart can be made based on the final EFV score. If (218) the final score is below a predetermined threshold, an arrhythmic rhythm is estimated (220). Using the variance sub-method, the AED 10 compares a threshold to the final EFV score to determine if the victim is in an arrhythmic state. Otherwise the processed signal is estimated to be normal. In one example, a preset threshold of 6 is used. In other examples, other preset thresholds can be used.

An arrhythmic sinus rhythm can be detected using the variance sub-method. These arrhythmic sinus rhythms can be different types of rhythms with different appropriate therapies. It may be difficult to distinguish between arrhythmic rhythms that are shockable rhythms and unshockable rhythms using only the variance sub-method. For example, VTs that are shockable (rates exceeding 120-150 beats per minute [BPM]) may not be distinguishable from non-shockable VTs (<120 BPM) solely with the measure from the variance sub-method. Thus, the quantification method preferably enhances the variance sub-method with at least one other spectral measurement in determining the appropriate therapy for detected sinus rhythms. The quantification method may also make decisions based on changes in the spectral parameters over time. Multiple measures may be thought of as forming a matrix, but actual implementations need not employ matrices.

In some implementations, the AED 10 may combine the frequency of the largest amplitude spectral peak (LASP) in the frequency spectrum with the measure from the variance sub-method to create a 1×2 matrix. In some implementations, AED 10 may additionally calculate the number of spectral peaks in the frequency representation of the ECG signal with amplitudes of at least 25% of the LASP using conventional methods known to those skilled in the art of signal processing and spectral analysis and include this measurement in the vector. A frequency of the LASP (FLASP) of less than 2 Hz and the number of peaks (NOP) less than 3 indicates that it is a shockable VT or VF, while a FLASP of greater than 2 Hz and an NOP of less than 3 indicates a non-shockable VT. Non-shockable supraventricular rhythms can have a NOP greater than 3.

In other implementations, the AED 10 can combine information from the variance sub-method and the FLASP and NOP measure, using information processing techniques described previously, to estimate the physiological state of the heart and suitable therapy. A combination of the EFV under a threshold and FLASP<2 Hz and NOP<3 can indicate a shockable VT or VF for which appropriate therapy can be defibrillation. A combination of the EFV under a threshold and FLASP>2 Hz and NOP<3 can indicate a non-shockable VT for which appropriate therapy can be normal CPR. A combination of the EFV under a threshold and NOP>3 can indicate a supraventricular rhythm for which appropriate therapy can be simply monitoring the patient or drug therapy.

A descriptor matrix may take the form of a [n×m] dimensional matrix, where n=the number of peaks and m=the number of parameters used to describe the spectral shape. In one implementation with m=6, the six parameters are the following: 1) the frequency of the particular peak (FP); 2) the amplitude of that peak (AP); 3) the width of the peak (PW); 4) the depth of the peak (DP); 5) the variance of that peak (VP); and 6) the first moment of that peak (FM). Peak number (PN) is a digit providing an identifier for each individual peak. For instance, initially the AED 10 detects 5 peaks, each PN numbered sequentially with frequencies at 1, 2, 3, 4, and 5 Hz. Four seconds later in time, however, the AED 10 detects a peak at a new frequency of 4.5 Hz and the peak is assigned a PN of 6.

The description matrix, which may be termed a spectral shape matrix (SSM), may include two header values, NOP and a boolean value, Gaussian peak (GP), which indicates that for spectral shapes that have a single peak (NOP=1) and GP=true, that the spectral shape may be described by a parameter subset of only FP, AP, and VP. The SSM may preferably take the form:

| | | | | |
|---|---|---|---|---|
| $FP_1$ | $AP_1$ | $PW_1$ | $VP_1$ | $FM_1$ |
| $FP_2$ | $AP_2$ | $PW_2$ | $VP_2$ | $FM_2$ |
| $FP_3$ | $AP_3$ | $PW_3$ | $VP_3$ | $FM_3$ |
| . | . | . | . | . |
| . | . | . | . | . |
| . | . | . | . | . |
| $FP_n$ | $AP_n$ | $PW_n$ | $VP_n$ | $FM_n$ |

Since fibrillation is a chaotic rhythm, the FP frequencies may vary at a rate faster than the time window of the short-time Fourier transform. For instance, if the time window for computing the Fourier transform to generate a frequency spectrum is set for 4 seconds, the FPs for adjacent time windows (and corresponding frequency spectrums) will appear to jump from one frequency to the next. If, however, the AED 10 applies a standard short time Fourier transform to the signal while at the same time increasing the rate at which a Fourier transform is performed on the incoming data, the time window will be reduced and thus there will be a loss in the spectral resolution of the Fourier transform. Thus, in one example, the AED 10 simultaneously performs multiple Fourier transforms on the ECG data with each subsequent transform initiated 400 milliseconds after initiation of the previous transform and a time window of 4 seconds, resulting in the AED performing 10 simultaneous transforms of data in a time window of 4 seconds. Thus, the data for each transform has some overlap with data for adjacent transforms. In such a manner, the AED 10 maintains both spectral and time resolution.

The AED 10 may calculate additional header values that describe generic aspects of the ECG spectrum. These additional header values may include, for instance, the amplitude spectrum area (AMSA) as described in U.S. Pat. No. 5,957,856 or the variance measure, as described previously. These values, along with NOP and GP, can be thought of as forming a vector on which matrix operations and transformations may be performed independently of, or combined with, the matrix formed by the parameters for the individual peaks.

The AED 10 can then perform matrix operations and transformations known to those skilled in the art on the SSM. The AED 10 can also calculate the SSM at regular intervals in time, to generate a [n×m×p] dimensional matrix, where p is the number of samples in the time interval of interest. Each SSM may be thought of as a point in [n, m]-space that then forms a trajectory in the [n, m, p]-space. The AED 10 then analyzes this trajectory to predict defibrillation success as well as to decide whether it is appropriate to defibrillate or deliver an alternative therapy such as chest compressions, drugs such as epinephrine, constitutive nutrients such as glucose, or other electrical therapy such as pacing.

The AED 10 may identify one or more peaks in the frequency spectrum. For each of these identified peaks, the AED 10 identifies a frequency band corresponding to the peak. The AED 10 may determine the peak model parameters, e.g. FP, AP, and PW, iteratively by a nonlinear parameter estimation or curve fitting routine for each peak's frequency band. For example, the AED 10 may use the Marquardt-Levenberg algorithm to minimize the error in the nonlinear parameter estimation or Chi-square, $\chi^2$, where $\chi^2$ is expressed as follows.

$$X^2(p) = \frac{1}{N-P}\sum_i\left[\frac{M(i)-S(i;p)}{\sqrt{M(i)}}\right]^2.$$

For this expression, there are N recorded energy values, M(i) are the recorded energy values, and S(i; p) is the synthesized model curve energy values, sampled at points i in dependence on p varying parameter values. The term enclosed in brackets corresponds to the normalized residuals R(i), which provide a weighted measure of the difference between the fit curve and the data at each measured frequency value M(i).

The AED 10 uses either the height-normalized Lorentzian function, L(E), or the Gaussian function, G(E) to model an energy function for each of the spectral peaks where E is a frequency. In the case of L(E):

$$L(E) = \left\{1 + \left[\frac{E-E_0}{\beta}\right]^2\right\}^{-1}.$$

In the case of G(E):

$$G(E) = \exp\left\{-\ln 2 \cdot \left[\frac{(E-E_0)}{\beta}\right]^2\right\}.$$

Both functions L(E), G(E) are completely characterized by the peak parameters β, corresponding to ½ the peak width at half-maximum peak amplitude and $E_0$, the peak position or FP. The AED 10 can model skew of the peak by combining the Gaussian G(E) and Lorentzian L(E), with β replaced by the term $\beta+\alpha(E-E_0)$. The AED 10 can also add in a factor h to allow for varying peak heights. The result is function ƒ(E). The AED 10 calculates ƒ(E) as follows.

$$f(E) = h\cdot\left\{1+M\cdot\left[\frac{E-E_0}{\beta+\alpha(E-E_0)}\right]^2\right\}^{-1}\cdot\exp\left\{(-1-M)\cdot\ln 2\cdot\left[\frac{E-E_0}{\beta+\alpha(E-E_0)}\right]^2\right\}$$

Some of the advantages of this product-type peak shape model ƒ(E) are the availability of analytical presentations of the partial derivatives of ƒ(E) with respect to the parameters, which are needed in the Marquardt-Levenberg algorithm to establish the Jacobi matrix, the analytical value of β, and a faster convergence of the iterative estimation process. The depth of each peak is estimated either by incorporating a baseline curve into the Marquardt-Levenberg algorithm, or by simply determining the two minimum points of the spectrum for a region around the estimated peak. Thus, using techniques known to one skilled in this art, the AED 10 can compute the spectral shape parameters of the peak: FP, AP, PW, DP, VP, and FM from the function ƒ(E).

If the AED 10 finds a peak in the immediately subsequent time interval for which the AP and FP value does not vary by more than preferably 10%, then that second peak is considered to have the same peak number, PN, indicating that it is the same peak with a shift in frequency and amplitude. In such a fashion, the AED 10 can develop trajectories for the parameters for each particular peak as well as for the overall descriptor matrix. The AED 10 can add a new peak at any time during the event, in which case the AED 10 gives the new peak a new PN value. If the AED 10 determines that a peak is extinguished, the PN number is maintained in memory of the AED 10. In the processing of candidates for new peaks, the sub-method reviews all extinguished peaks to first determine if the new peak is actually an extinguished peak, in which case the candidate is not given a new PN, and instead is given the PN number of the extinguished peak.

Prior to a successful shock of a heart in a dangerous rhythm, one or more parameters AP, DP, VP, FP, PW of peaks in the 6-12 Hz range of the frequency spectrum can oscillate with a cycle rate in the range of 0.1-1 Hz. Thus, detection of this oscillation through multiple time windows and frequency spectrums can be incorporated into the information processing technique as an additional sub-method that can recommend defibrillating the heart. Furthermore, the sub-method can recommend timing the defibrillating shock when the peaks are at a maximum energy in the 0.1-1 Hz cycle. For example, the sub-method can recommend timing the delivery of the defibrillation shock to occur during the 100 millisecond Fourier transform cycle when the APs in the 6-12 Hz region are at a maximum. When the particular AP-maximum cycle has be found, the AED 10 waits to deliver the defibrillation shock until the AED 10 detects the peak of the waveform after it has been band pass-filtered with a center frequency of 7 Hz. This sub-method synchronizes the shock with the elements of the ECG waveform that are most related to the normal sinus QRS.

Figure 7A:
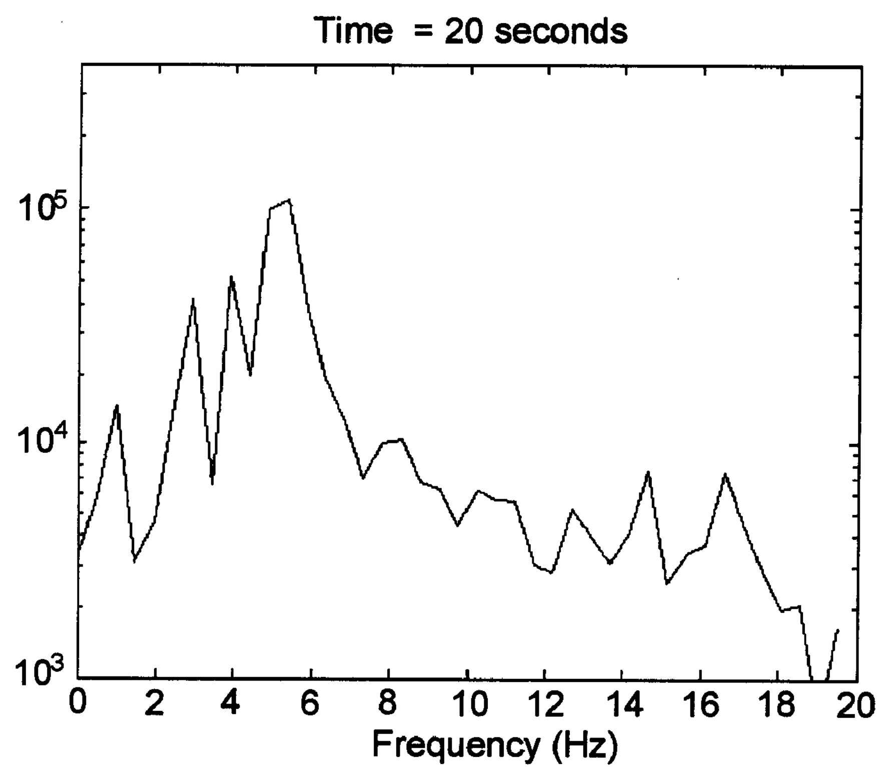
FIG. 7A and 7B are examples of an ECG spectrum at two points in time, in this case separated by 4 seconds.
Figure 7B:
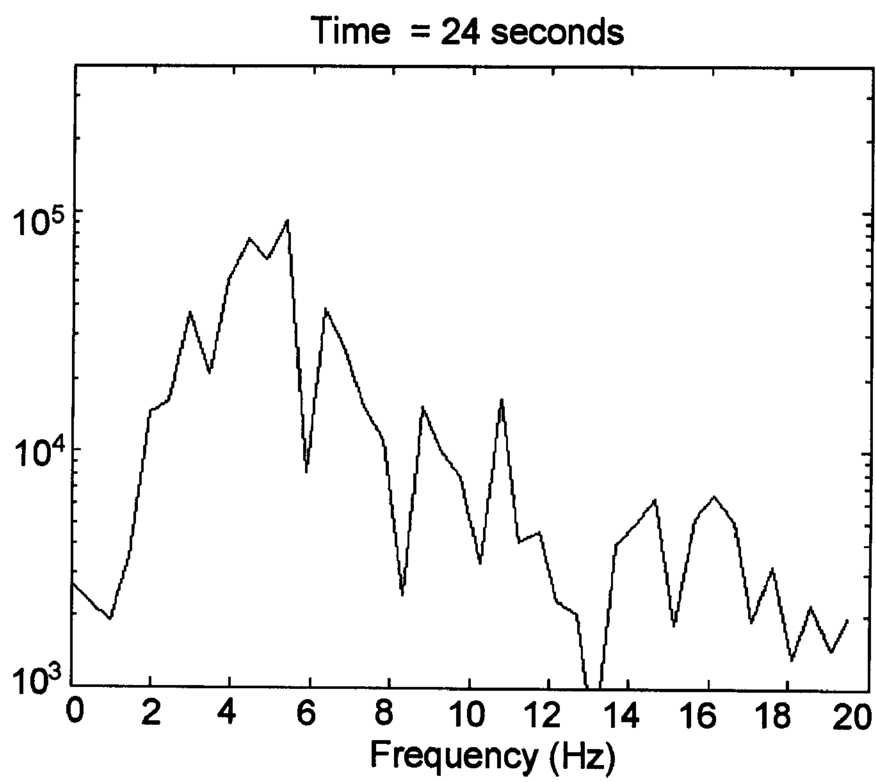

The parameters FP, AP, and PW of peaks in the 6-12 Hz region may also undergo oscillations indicating a change in the state of the heart as shown in FIGS. 7A and 7B, which depict the spectrum as measured at two points in time, separated by an interval of 4 seconds. For a heart that has been in fibrillation for a period of time, the ECG undergoes a gradual degradation in the values of the parameters FP, AP, and PW of peaks in the 6-12 Hz region of the frequency spectrum. As described previously, suitable therapy for a heart that has been in fibrillation for a period time is to do chest compressions and then defibrillate. This degradation is measured over at least a 8-10 second interval. This is an additional sub-method for the information processing technique. For example, if the AED 10 detects the APs of at least two peaks in the 6-12 Hz region of the frequency spectrum decreasing by at least 15% over a 10 second interval, the sub-method recommends chest compressions and then defibrillation.

If the circulation and metabolic substrate of the heart improve to the point that the heart is more likely to be able to recover from a defibrillation shock, changes in the parameters FP, AP, and PW of peaks in the 6-12 Hz region of the frequency spectrum will provide precursors to changes in the ECG that might be seen in the time domain of the ECG signal, such as an increase in the amplitude of the ventricular fibrillation ECG (often termed "coarsening" by medical practitioners). If the AED 10 detects an increase in the parameters FP, AP, DP, VP or PW of peaks in the 6-12 Hz region of the frequency spectrum, for instance as shown in FIG. 7B, a sub-method will recommend ceasing chest compressions or other current therapy and then defibrillation.

The peak frequencies, FP, for the peaks in the 6-12 Hz region of the frequency spectrum can vary over time less when the condition of the heart is improving and thus the heart can handle the shock of defibrillation. This may be due to the presence in the myocardial activations of more normal activity at low levels manifesting in harmonics of the sinus rhythm fundamental frequency. This variation in the peak frequencies may be measured as the ratio of the average change in frequency in the region of 6-12 Hz with that of the FPs in the frequency range of 3-6 Hz or measured as an absolute change for FPs in the range of 6-12 Hz. This sub-method, upon detecting the variation in the peak frequencies, recommends defibrillation to the information processing technique.

It is also possible for a sub-method to project the [n×m×p] trajectory of the SSM matrix onto a plane within the [n×m]-space and then analyze the form taken by the projection of the trajectory in the plane to determine the appropriate time to shock or the optimal treatment. The projection may include up to (n+m) variables of different weightings, though it preferably is a projection that is primarily along the VP axis of the [n×m]-space. In the plane projection, image mensuration algorithms are employed to evaluate the features of the two dimensional projection of the trajectory. The following are some of the preferred mensuration classes for which measurements are made by means known to those skilled in the art: area, centroid, circularity, clustering, compactness, maximum axis, minimum axis, and perimeter. For instance, the minimum axis may be determined as follows. The minimum axis of an object is formally defined as the axis of maximum inertia (dispersion) passing through the centroid. One method to calculate the minimum axis is to compute the eigenvalues and eigenvectors of the scatter matrix comprised of the coordinate points of the object. The eigenvector corresponding to the smallest eigenvalue is the minimum axis. Another method is to fit an ellipse to the object perimeter.

The projection may be calculated for a specific duration of time, for instance 10 seconds, resulting in a series of 2-dimensional objects that are representations of the trajectory in time—so-called projection "snap-shots". It then becomes possible to analyze trends in the time series of values in the mensuration classes for changes indicative of improving physiological conditions. For instance, an increased amplitude in VP oscillation during VF is indicative of an improving physiological state. In this case, the AED 10 would then provide feedback to the caregiver to continue performing the rescue operation as they have with an audible prompt such as, “Keep up the good work. The patient’s condition is improving.” Other such mensuration classes that are of value to track over time are the maximum axis angle, the perimeter and compactness.

Methods such as the Kalman filter may be used for the estimation and prediction of the trajectory. The Kalman filter estimates a process by using a form of feedback control: the filter estimates the process state at some time and then obtains feedback in the form of (noisy) measurements. As such, the equations for the Kalman filter fall into two groups: time update equations and measurement update equations. The time update equations are responsible for projecting forward (in time) the current state and error covariance estimates to obtain the a priori estimates for the next time step. The measurement update equations are responsible for the feedback—i.e. for incorporating a new measurement into the a priori estimate to obtain an improved a posteriori estimate. The time update equations can also be thought of as predictor equations, while the measurement update equations can be thought of as corrector equations. Indeed the final estimation algorithm resembles that of a predictor-corrector algorithm for solving numerical problems.

Discrete Kalman filter time update equations:

$$\hat{x}_k^- = A\hat{x}_{k-1} + Bu_{k-1}$$

$$P_k^- = AP_{k-1}A^T + Q$$

Discrete Kalman filter measurement update equations:

$$K_k = P_k^- H^T (HP_k^- H^T + R)^{-1}$$

$$\hat{x}_k = \hat{x}_k^- + K_k(z_k - H\hat{x}_k^-)$$

$$P_k = (I - K_k H)P_k^-$$

The first task during the measurement update is to compute the Kalman gain, $K_k$. The next step is to actually measure the process to obtain, and then to generate an a posteriori state estimate by incorporating the measurement, $z_k$. The final step is to obtain an a posteriori error covariance estimate, $P_k$. After each time and measurement update pair, the process is repeated with the previous a posteriori estimates used to project or predict the new a priori estimates. This recursive nature is one of the very appealing features of the Kalman filter—it makes practical implementations much more feasible than (for example) an implementation of a Wiener filter which is designed to operate on all of the data directly for each estimate. The Kalman filter instead recursively conditions the current estimate on all of the past measurements. The equation, $$\hat{x}_k = \hat{x}_k^- + K_k(z_k - H\hat{x}_k^-)$$

is termed the predictor equation.

One of the primary limitations of the Kalman filter is that it only models a linear system with Gaussian distribution, not often encountered in the physiological setting. The best known algorithm to solve the problem of non-Gaussian, nonlinear filtering is the extended Kalman filter (EKF). This filter is based upon the principle of linearizing the measurements and evolution models using Taylor series expansions. The series approximations in the EKF algorithm can, however, lead to poor representations of the nonlinear functions and probability distributions of interest. As a result, this filter can diverge. Based on the hypothesis that it is easier to approximate a Gaussian distribution than it is to approximate arbitrary nonlinear functions other researchers have developed a filter termed the unscented Kalman filter (UKF). It has been shown that the UKF leads to more accurate results than the EKF and that in particular it generates much better estimates of the covariance of the states (the EKF often seems to underestimate this quantity). The UKF has, however, the limitation that it does not apply to general non-Gaussian distributions as is often the case with the ECG spectral distributions. Sequential Monte Carlo methods, also known as particle filters overcome this limitation and allow for a complete representation of the posterior distribution of the states, so that any statistical estimates, such as the mean, modes, kurtosis and variance, can be easily computed. Particle Filters can therefore, deal with any nonlinearities or distributions. Particle filters rely on importance sampling and as a result, require the design of proposal distributions that can approximate the posterior distribution reasonably well. In general, it is hard to design such proposals. The most common strategy is to sample from the probabilistic model of the states evolution (transition prior). This strategy can, however, fail if the new measurements appear in the tail of the prior or if the likelihood is too peaked in comparison to the prior.

In the preferred implementation, a estimator/predictor trajectory tracking technique known as the unscented Particle Filter (UPF) as developed by Merwe, Doucet, Freitasz and Wan. Pseudocode for the UPF is as follows:

Unscented Particle Filter:

Initialization: t=0.

For i=1, . . . N, draw states (particles) $x_0^{(i)}$ from the prior $p(x_0)$ and set, $$\bar{x}_0^{(i)} = E[x_0^{(i)}]$$

$$P_0^{(i)} = E\left[(x_0^{(i)} - \bar{x}_0^{(i)})(x_0^{(i)} - \bar{x}_0^{(i)})^T\right]$$

$$\bar{x}_0^{(i)a} = E[x^{(i)a}] = \left[(\bar{x}_0^{(i)})^T \;\; 0 \;\; 0\right]^T$$

$$P_0^{(i)a} = E\left[(x_0^{(i)a} - \bar{x}_0^{(i)a})(x_0^{(i)a} - \bar{x}_0^{(i)a})^T\right] = \begin{bmatrix} P_0^{(i)} & 0 & 0 \\ 0 & Q & 0 \\ 0 & 0 & R \end{bmatrix}$$

For t=1,2, . . . , a) Importance sampling step:

For i=1, . . . N: Update particles with the UKF:

Calculate sigma points:

$$\mathcal{X}_{i-1}^{(i)a} = \left[\bar{x}_{i-1}^{(i)a} \;\; \bar{x}_{i-1}^{(i)a} \pm \sqrt{(n_a + \lambda)P_{i-1}^{(i)a}}\right]$$

Predict future particle (time update)

$$\mathcal{X}_{i|t-1}^{(i)x} = f(\mathcal{X}_{t-1}^{(i)x}, \mathcal{X}_{t-1}^{(i)x}) \qquad \bar{x}_{i|t-1}^{(i)} = \sum_{j=0}^{2n_x} W_j^{(m)} \mathcal{X}_{j,i|t-1}^{(i)x}$$

$$P_{i|t-1}^{(i)} = \sum_{j=0}^{2n_x} W_j^{(a)} [\mathcal{X}_{j,i|t-1}^{(i)x} - \bar{x}_{i|t-1}^{(i)}][\mathcal{X}_{j,i|t-1}^{(i)x} - \bar{x}_{i|t-1}^{(i)}]^T$$

$$\mathcal{Y}_{i|t-1}^{(i)} = h(\mathcal{X}_{i|t-1}^{(i)x}, \mathcal{X}_{t-1}^{(i)n}) \qquad \bar{y}_{i|t-1}^{(i)} = \sum_{j=0}^{2n_x} W_j^{(m)} \mathcal{Y}_{j,i|t-1}^{(i)}$$

Incorporate new observation (measurement update)

$$P_{\overline{y}_i\overline{y}_t} = \sum_{j=0}^{2n_x} W_j^{(a)}[\mathcal{Y}_{j,i|t-1}^{(i)} - \overline{y}_{i|t-1}^{(i)}][\mathcal{Y}_{j,i|t-1}^{(i)} - \overline{y}_{i|t-1}^{(i)}]^T$$

$$P_{x_i y_t} = \sum_{j=0}^{2n_x} W_j^{(a)}[\mathcal{X}_{j,i|t-1}^{(i)} - \overline{x}_{i|t-1}^{(i)}][\mathcal{Y}_{j,i|t-1}^{(i)} - \overline{y}_{i|t-1}^{(i)}]^T$$

$$K_t = P_{x_i y_t} P_{\overline{y}_i\overline{y}_t}^{-1} \qquad \overline{x}_i^{(i)} = \overline{x}_{i|t-1}^{(i)} + K_t(y_i - \overline{y}_{i|t-1}^{(i)})$$

$$\hat{P}_i^{(i)} = P_{i|t-1}^{(i)} - K_t P_{\overline{y}_i\overline{y}_t} K_t^T$$

– Sample $\hat{x}_t^{(i)} \sim q(x_t^{(i)} \mid x_{0:t-1}^{(i)},, y_{1:t}) = \mathcal{N}(\hat{x}_t^{(i)}, \hat{P}_t^{(i)})$ – Set $\hat{x}_{0:t}^{(i)} \triangleq (x_{0:t-1}^{(i)}, \hat{x}_t^{(i)})$ and $\hat{P}_{0:t}^{(i)}(P_{0:t-1}^{(i)}, \hat{P}_t^{(i)})$ For i=1, . . . N, evaluate the importance weights up to a normalizing constant:

$$w_t^{(i)} \propto \frac{p(y_t \mid \hat{x}_t^{(i)})p(\hat{x}_t^{(i)} \mid x_{t-1}^{(i)})}{q(\hat{x}_t^{(i)} \mid x_{0:t-1}^{(i)}, y_{1:t})}$$

For i=1, . . . N, normalize the importance weights.

b) Selection Step

Multiply/Suppress particles, $(\hat{x}_{0:t}^{(i)}, \hat{P}_{0:1}^{(i)})$ with high/low importance weights, $\tilde{w}_t^{(i)}$ respectively, to obtain N random particles.

c) Output: The output of the algorithm is a set of samples that can be used to approximate the posterior distribution as follows:

$$p(x_{0:t} \mid y_{1:t}) \approx \hat{p}(x_{0:t} \mid y_{1:t}) = \frac{1}{N}\sum_{i=1}^{N} \delta_{(x_{0:1}^{(i)})}(dx_{0:1})$$

Resulting in the estimate of, $$E(g_i(x_{0:t})) = \int g_t(x_{0:t})\, p(x_{0:1} \mid y_{1:t}) dx_{0:1} \approx \frac{1}{N}\sum_{i=1}^{N} g_i(x_{0:t}^{(i)})$$

for some function of interest, $g_t$, for instance the marginal conditional mean or the marginal conditional covariance or other moment.

In one implementation the prediction matrix may be used to anticipate the optimal therapeutic intervention. Rather than wait for the characteristics of the parameters or trajectory to achieve a certain condition, the algorithm will base its output on the predicted future state of the patient using the tracking and prediction algorithms mentioned above.

Transform methods other than the Fourier method may be employed, for instance the Laplace, Hilbert, Radon, and Hankel transforms, as well as time frequency transforms such as the Gabor short time Fourier transform and the Wavelet transform.

Other data besides ECG data may be included as part of the description matrix and incorporated into the analysis algorithm, for instance pulse oximetry, capnography, respiration, impedance cardiography and blood pressure measurements. At least some of the data may remain in the time domain without any Fourier or other transform method being performed on it. Pulse oximetry, impedance cardiography, and blood pressure measurements may be used to augment the ECG to determine if a pulse is present. Capnography may be used to determine the overall effectiveness of cardiopulmonary resuscitation.

Large (~5" in diameter), self-adhesive electrode pads are typically used to deliver defibrillation therapy to patients. The pads also provide ECG monitoring through the same conductive surfaces. In one implementation, additional small (~0.5" diameter) ECG electrodes are integrated into the large pads that provide simultaneous monitoring of at least one additional electrical vector that is approximately orthogonal to the monitoring vector produced by the large defib/monitoring electrodes. A second matrix is then formed, identical in structure to the original SSM, but based on the orthogonal leads. The AED 10 can then perform techniques such as cross correlation on the two matrices to verify state changes.

In one embodiment, the two small ECG electrodes and large pads are configured such that there at least two mutually orthogonal ECG leads are generated. The vector sum of these leads generates a trajectory over time. The same methods for trajectory analysis described above may be used to analyze this trajectory as well.

As described previously, the AED 10 combines these sub-methods to determine appropriate therapy for the rescuer to perform on the victim. If uncertainty is included in the combination, the probability of defibrillation success is shown on the display of the device as a number between zero and one hundred, allowing the trained medical person such as a paramedic to make his own decision as to whether to shock the patient. In an implementation where the variance sub-method is used, the AED 10 may be configured such that the VF detection algorithm employing spectral variance may provide notification in the form of an audible or visual alarm indication that the paramedic should stop doing compressions for a more accurate analysis of the ECG waveform. In a more automated implementation, if the AED 10 determines that defibrillation has a low probability of success, the AED 10 may prompt the rescuer to perform CPR. During the course of CPR, the AED 10 may analyze the ECG continuously and prompt the rescuer to cease doing CPR when the AED 10 determines that the myocardium will be receptive to defibrillation. Following the defibrillation, the AED 10 may prompt the rescuer to deliver uninterrupted chest compressions, and the AED 10 may again monitor the underlying ECG waveform during compressions for the appropriate time to deliver the defibrillation therapy. As a result of the spectral analysis, the AED 10 may also determine that neither defibrillation nor CPR is appropriate, but rather drug and metabolic therapy such as epinephrine and glucose is appropriate, in which case the AED 10 will prompt the rescuer to deliver the appropriate therapy.

In another embodiment for determining the appropriate treatment for a victim, the frequency domain of the ECG signal is divided into spectral bands. For example, the frequency range of 3-20 Hz may be divided into 0.1 Hz bands. The energy for each band is calculated, and individual weights are assigned to the energy values for each of the bands. In one embodiment, a summation of at least some of the weighted energy values for each band is calculated.

Regression analysis may be used to determine weights that produce improved correlation between the weighted sum and the probability of successful defibrillation (or between the weighted sum and the presence of a physiological condition). The model for simple linear regression is:

$Y=a+b*X$ where Y is the dependent variable, X is the independent variable, and a and b are the regression parameters (the intercept and the slope of the line of best fit). The model for multiple linear regression is:

$Y=a+b_1*X_1+b_2*X_2+\ldots+b_i*X_i$

The coefficients, $b_i$, for each energy, $X_i$, are calculated using statistical methods such as the general linear model to provide a best estimate of the probability of defibrillation success, Y. The variable, Y, may also represent the probability of success of any therapeutic intervention other than defibrillation, for instance chest compressions, ventilations or a metabolic treatment such as epinephrine or aspartate. The variable, Y, may also represent the probability that the patient is in a particular physiological state. The general linear model (GLM) can estimate and test any univariate or multivariate general linear model, including those for multiple regression, analysis of variance or covariance, and other procedures such as discriminant analysis and principal components. With the general linear model, randomized block designs, incomplete block designs, fractional factorial designs, Latin square designs, split plot designs, crossover designs, nesting, can be explored. The model is:

$Y=XB+e$ where Y is a vector or matrix of dependent variables, X is a vector or matrix of independent variables, B is a vector or matrix of regression coefficients, and e is a vector or matrix of random errors.

In multivariate models, Y is a matrix of continuous measures. The X matrix can be either continuous or categorical dummy variables, according to the type of model. For discriminant analysis, X is a matrix of dummy variables, as in analysis of variance. For principal components analysis, X is a constant (e.g., a single column of 1s). For canonical correlation, X is usually a matrix of continuous right-hand variables (and Y is the matrix of left-hand variables).

For some multivariate models, it may be easier to use ANOVA, which can handle models with multiple dependent variables and zero, one, or more categorical independent variables (that is, only the constant is present in the former). ANOVA automatically generates interaction terms for the design factor.

After the parameters of a model have been estimated, they can be tested by any general linear hypothesis of the following form:

ABC'=D where A is a matrix of linear weights on coefficients across the independent variables (the rows of B), C is a matrix of linear weights on the coefficients across dependent variables (the columns of B), B is the matrix of regression coefficients or effects, and D is a null hypothesis matrix (usually a null matrix).

The coefficients, $b_i$, are calculated using ECG or other measured physiological data collected from a statistically varied population of samples to provide a robust database for accurate model generation. Preferably, the resuscitation event is decomposed into multiple therapy states, e.g., arrival at patient's side, pre-shock, post-shock, post-vasopressor, etc., with separate sets of coefficients generated for each therapy state. The state of therapy, e.g., resuscitation, is determined and stored by the defibrillator. For instance when the unit is first turned on and prior to the first shock, the resuscitation is considered in the "arrival at patient's side" (APS) state; if CPR is detected by the defibrillator, it shifts to the "CPR first, no shock state"; after defibrillation, the state machine shifts to the "first shock" state. Subsequent shocks cause the state machine to transition to states for each defibrillation, e.g. "second shock", etc. Coefficients, $b_i$, are calculated for each state and stored on the defibrillator, and used to calculate the most accurate predictor, Y, of therapeutic outcome (or current physiologic state). Therapeutic outcome, Y, may be scaled so as to provide a value from either zero to one or zero to one-hundred, representing on a scale that is understandable to the operator that it is a probability; the value of Y may also be unscaled.

Regression may also be performed using the logistic function:

$$Y = 100\left[1 - \frac{1}{1 + e^{b_o + \Sigma b_i x_i}}\right]$$

Figure 8:
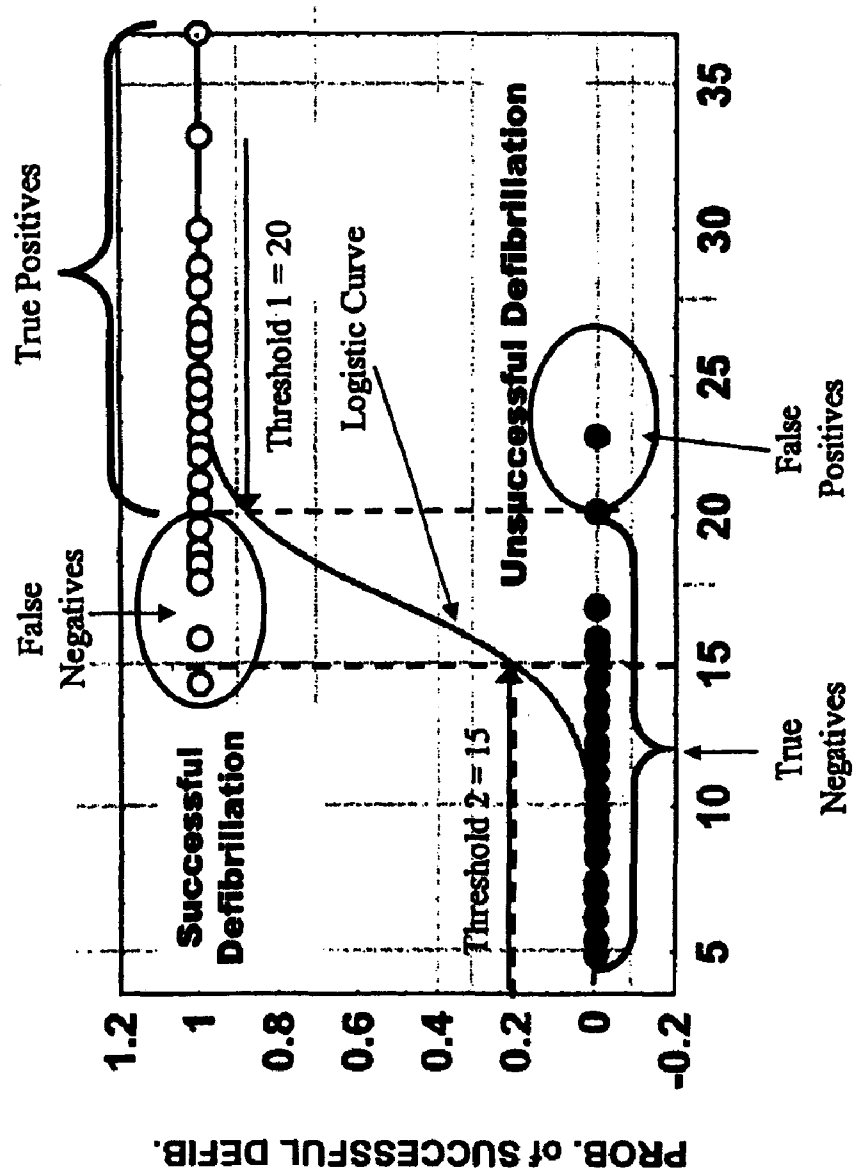
FIG. 8 shows a logistic curve that relates a measured predictive variable (x axis) into a approximate probability of therapeutic success (y axis).

The logistic model is useful in estimating the probability of therapeutic success where the outcome is binomial and dependent on at least one predictive factor, plotted on the abscissa of FIG. 8, such that certain values of the predictive factor, e.g. 16 in FIG. 8, will sometimes be associated with successful defibrillation and other times with unsuccessful defibrillations. The logistic curve is a non-linear transformation that converts the measured predictive factor into a value approximating a probability of success. It provides a reasonable, mathematically tractable approach to minimizing the false negatives and false positives, as shown in FIG. 8. A threshold is chosen that typically will optimize both the false negatives (FN) and false positives (FP) to provide the best sensitivity and specificity for the prediction:

Sensitivity=True Positives $(TP)/(TP+FN)$

Specificity=$TN/(TN+FP)$

Positive Predictive Value $(PPV)=TP/(TP+FP)$

Negative Predictive Value $(NPV)=TN/(TN+FN)$

However, depending on the therapy stage, it may be desirable to optimize for reduction in false positives at the expense of additional false negatives. For instance, when medical personnel first arrive at the side of a patient, it has been shown in several studies that it is beneficial to many patients that some period of time, typically on the order of 2-3 minutes, is spent performing cardiopulmonary resuscitation such as chest compressions and artificial breathing prior to defibrillation. This has been coined "CPR-first", and runs counter to how resuscitation of cardiac arrest has been taught for over a decade. One difficulty with the method is that for cardiac arrest victims for whom the onset is more recent, typically on the order of 4 minutes or less, the clinical data suggests that defibrillation first is a more efficacious therapy for that class of patient. In this case, a "true negative" is an instance when the predictive factor (or measured parameter) is below the threshold and the outcome was an unsuccessful defibrillation. Because defibrillation is necessary to convert ventricular fibrillation, but shocking unnecessarily while not delivering effective CPR is deleterious and decreases the chances of survival, it is important to minimize as much as possible the number of patients in the false negative group since these are patients who would have done better had they been shocked first rather than having CPR-first performed on them. Choosing a threshold in the range of 13-15 will result in a Negative Predictive Value (NPV) of nearly 100%. Thus the rescuer would only do CPR-first on those patients for whom there was a very high likelihood that CPR will do better than defibrillation.

On the other hand, at a later therapy stage (later on in the resuscitation), after an unsuccessful defibrillation shock, doing continuous, uninterrupted CPR becomes critical to the survival of the patient. Thus, it is undesirable to have the rescuer stopping to perform potentially unsuccessful defibrillations. In this resuscitation state, minimizing false positives becomes of primary importance. Raising the threshold to approximately 20 will result in a Positive predictive Value (PPV) of nearly 100%.

Other therapy stages for which specific thresholds can be set can be based on the ECG rhythm state of the patient, such as asystole, ventricular fibrillation, ventricular tachycardia, or pulseless electrical activity.

Therapy stage may also be determined by providing the device with a means of detecting whether or not the rescuer is performing chest compressions or ventilations, e.g., by monitoring an accelerometer-based sensor mounted on the patient's sternum or by measuring the transthoracic impedance of the patient, such as is done by the AED Pro defibrillator manufactured by ZOLL Medical (Chelmsford Mass.).

Therapy stage may also be determined from data that the rescuer enters into the device. The device may also have a means for the rescuer to enter treatment data into the device in real time; such data might include whether or not any of the following treatments had been given to the patient (though not limited to): epinephrine or other vasopressor, levosimendan, aspartate, glucose, intubation, external chest compressor device, glucose. Treatment data input may be by keying means such as on the ZOLL Medical (Chelmsford, Mass.) M-Series or E-Series defibrillators. Treatment modes such as pacing and defibrillation can be distinguished if there is a rotary machine operation dial or knob to set the unit to mutually exclusive operational modes such as pacing, monitoring, or defibrillation. Other modes might include fluid infusion or ventilation.

A state transition matrix can be developed using a Markov model and the threshold adjusted as well as different weighting coefficients applied based on the Markov model estimation. In particular, the sequence of medical interventions and patient reactions to treatments is modeled as a hidden Markov model (HMM), defined as a variant of a finite state machine having a set of states, Q, an output alphabet, O, transition probabilities, A, output probabilities, B, and initial state probabilities, Π. The current state is not observable. Instead, each state produces an output with a certain probability (B). Usually the states, Q, and outputs, O, are understood, so an HMM is said to be a triple, λ=(A, B, Π). Each value of output alphabet, O, can be given a unique threshold and coefficient set.

$A=\{a_{ij}=P(q_j \text{ at } t+1 | q_i \text{ at } t)\}$, where P(a|b) is the conditional probability of a given b, $t \geqq 1$ is time, and $q_i \in Q$.

Informally, A is the probability that the next state is $q_j$ given that the current state is $q_i$.

$B=\{b_{ik}=P(o_k|q_i)\}$, where $o_k \in O$.

Informally, B is the probability that the output is $o_k$ given that the current state is $q_i$.

$\Pi=\{p_i=P(q_i \text{ at } t=1)\}$.

The Forward-Backward and Baum-Welch algorithms are performed on a database to build the HMM. A global HMM is developed for all medical modes along with specific HMMs for each mode such as pacing, defibrillation, etc.

The Forward-Backward algorithm may be summarized as follows:

Define the α values as follows,

α_t(i)=Pr(O_1=o_1, . . . ,O_t=o_t, X_t=q_i|λ)

Note that $$\alpha\_T(i) = Pr(O\_1 = o\_1, \ldots , O\_T = o\_T, X\_T = q\_i \mid \lambda) = Pr(\sigma, X\_T = q\_i \mid \lambda)$$

The alpha values enable us to solve Problem 1 since, marginalizing, we obtain $$Pr(\sigma \mid \lambda) = sum\_i = 1\hat{}N\ Pr(o\_1, \ldots , o\_T, X\_T = q\_i \mid \lambda) = sum\_i = 1\hat{}N\ \alpha\_T(i)$$

Define the β values as follows,

β_t(i)=Pr(O_t+1=o_t+1, . . . ,O_T=o_T|X_t=q_iλ)

1. Compute the forward (α) values:

α_1(i)=pi_i b_i(o_1) a.

α_t+1(j)=[sum_i=1^N α_t(i)a_ij]b_j(o_t+1) b.

2. Computing the backward (β) values:

β_T(i)=1 a.

β_t(i)=sum_j=1^Na_ij b_j(o_t+1)β_t+1(j) b.

The Baum-Welch algorithm may be summarized as follows:

The probability of a trajectory being in state q_i at time t and making the transition to q_j at t+1 given the observation sequence and model.

xi_t(i,j)=Pr(X_t=q_i, X_t+1=q_j|σ,λ)

These probabilities may be computed using the forward backward variables.

$$xi\_t(i, j) = \frac{\alpha\_t(i)\, a\_ij(o\_t+1)\, \beta\_t+1(j)}{Pr(O \mid \lambda)}$$

The probability of being in q_i at t given the observation sequence and model.

gamma_t(i)=Pr(X_t=q_i|σ,λ)

Which we obtain by marginalization.

γ_t(i)=sum_j xi_t(i,j)

Note that sum_t=1^T γ_t(i)=expected number of transitions from q_i and sum_t=1^T xi_t(i,j)=expected number of transitions from q_i to q_j The algorithm is as follows:

1. Choose the initial parameters, λ, arbitrarily.
2. Reestimate the parameters.

a. $bar\{\pi\}\_i = \gamma\_t(i)$ b. $bar\{a\}\_ij = \dfrac{sum\_t = 1\hat{}T - 1\ xi\_t(i, j)}{sum\_t = 1\hat{}T - 1\ \gamma\_t(i)}$ -continued c. $$\text{bar}\{b\}\_\text{j}(k) = \frac{\text{sum\_t} = 1\,\hat{}\,T - 1\ \gamma\_\text{t}(j)\ 1\_\{\text{o\_t} = k\}}{\text{sum\_t} = 1\,\hat{}\,T - 1\ \gamma\_\text{t}(j)}$$

where 1_{o_t = k} = 1 if o_t = k and 0 otherwise.

3. Let bar{A}={bar{a}_ij)}, bar{B}={bar{b}_i(k)}, and bar{π}={{bar{π}_i}.

4. Set bar{λ} to be {bar{A}, bar{B}, bar{λ}}.

5. If λ=bar{λ} then quit, else set λ to be bar{λ} and return to Step 2.

Based on the state transition probabilities calculated by the Baum-Welch algorithm, the Viterbi algorithm may be used to provide a best estimate of the future sequence of medical interventions that the user will input.

The Viterbi algorithm may be summarized as follows:

1. Initialization:

For 1<=i<=N, a. δ__1(i)=πb_i(o__1)

b. Φ__1(i)=0

2. Recursion:

For 2<=t<=T, 1<=j<=N, a. δ__t(j)=max__i[δ_t−1(i)a_ij]b_j(o_t)

b. Φ_t(j)=argmax_i[δ_t−1(i)a_ij]

3. Termination:

a. p*=max_i[δ_T(i)]

b. i*_T=argmax_i[δ_T(i)]

4. Reconstruction:

For t=t−1,t−2, . . . ,1, i*_t=(Φ_t+1(i*_t+1)

The resulting trajectory, i*__1, . . . , i*_t+1, predicts the next likely intervention, based on the previous sequence.

Many other implementations of the invention other than those described above are within the invention, which is defined by the following claims.

What is claimed is:

1. A method of automatically determining which type of cardiac resuscitation treatment is most appropriate for a patient, the method comprising:

transforming one or more time domain ECG signal measurements from the patient into frequency domain data representative of the frequency content of the time domain measurements;

processing the frequency domain data to form a plurality of spectral bands, the content of each of the spectral bands representing the frequency content of the measurements within a different frequency band;

forming a weighted sum of the content of the spectral bands, with different weighting coefficients applied to at least some of the different spectral bands, wherein the magnitudes of the weighting coefficients are not linearly proportional to the frequency of the spectral band to which they are applied;

determining the type of cardiac resuscitation treatment based on the weighted sum.

2. The method of claim 1 wherein the weighting coefficients are ones chosen using a regression analysis comparing actual time domain measurements and actual outcome of therapy for a population of patients.

3. The method of claim 2 wherein the weighting coefficients have been chosen to improve a correlation between the weighted sum and the outcome of therapy.

4. The method of claim 1 wherein the weighting coefficients are different for at least two different therapy stages.

5. The method of claim 4 wherein the therapy stages comprise at least arrival at patient's side, pre-shock, and post-shock.

6. The method of claim 5 wherein therapy stage is based at least in part on rescuer entered data indicative of at least what drugs have been delivered to the patient.

7. The method of claim 6 wherein the rescuer entered data is further indicative of whether the patient has been intubated, and whether an automatic external chest compressor has been used.

8. The method of claim 1 wherein the determining comprises comparing weighted sum to a threshold.

9. The method 8 wherein the threshold is different for at least two therapy stages.

10. The method of claim 9 wherein if the weighted sum exceeds the threshold the type of treatment determined to be appropriate is delivery of a defibrillation shock.

11. The method of claim 10 wherein, when the therapy stage is arrival at the patient's side, the threshold used is lower than the threshold used for later therapy stages.

12. The method of claim 1 wherein the weighted sum for a normal sinus rhythm is significantly less than the weight sum for ventricular fibrillation.

13. The method of claim 1 wherein the spectral bands have a bandwidth of about 0.5 Hz.

14. The method of claim 1 wherein the spectral bands have a bandwidth of about 0.25 Hz.

15. The method of claim 1 wherein the spectral bands have a bandwidth of about 0.10 Hz.

16. The method of claim 15 wherein the spectral bands comprise adjacent frequency bands extending from about 3 Hz to about 20 Hz.

17. The method of claim 1 wherein the spectral bands have a bandwidth of about 1.0 Hz or less.

18. The method of claim 1 wherein the spectral bands have a bandwidth of about 0.5 Hz or less.

19. The method of claim 18 wherein the spectral bands comprise adjacent frequency bands extending from about 3 Hz to about 12 Hz.

20. The method of claim 1 wherein the spectral bands comprise adjacent frequency bands extending from about 3 Hz to about 12 Hz.

21. The method of claim 1 wherein the spectral bands comprise adjacent frequency bands extending from about 3 Hz to about 20 Hz.

22. The method of claim 1 wherein determining the type of cardiac resuscitation treatment comprises determining a probability that a defibrillation shock will be successful.

23. The method of claim 1 wherein determining the type of cardiac resuscitation treatment comprises determining whether to continue CPR or to deliver a defibrillation shock.

* * * * *

UNITED STATES PATENT AND TRADEMARK OFFICE

CERTIFICATE OF CORRECTION

PATENT NO. : 8,165,671 B2
APPLICATION NO. : 11/136327
DATED : April 24, 2012
INVENTOR(S) : Gary A. Freeman et al.

It is certified that error appears in the above-identified patent and that said Letters Patent is hereby corrected as shown below:

Column 28, line 18, after “method” insert -- of claim --.

Signed and Sealed this
Seventeenth Day of July, 2012

David J. Kappos
*Director of the United States Patent and Trademark Office*

UNITED STATES PATENT AND TRADEMARK OFFICE

CERTIFICATE OF CORRECTION

PATENT NO. : 8,165,671 B2
APPLICATION NO. : 11/136327
DATED : April 24, 2012
INVENTOR(S) : Gary A. Freeman and James E. Brewer It is certified that error appears in the above-identified patent and that said Letters Patent is hereby corrected as shown below:

Title Page, add -- item [60] “Related U.S. Application Data” – Provisional application No. 60/674,175, filed on 04/22/2005. --

Signed and Sealed this
Twenty-fourth Day of June, 2014

Michelle K. Lee

Michelle K. Lee
*Deputy Director of the United States Patent and Trademark Office*